(12) United States Patent
Voronov et al.

(10) Patent No.: US 11,959,057 B2
(45) Date of Patent: Apr. 16, 2024

(54) AUTOMATED ADDRESSABLE MICROFLUIDIC TECHNOLOGY FOR MINIMALLY DISRUPTIVE MANIPULATION OF CELLS AND FLUIDS WITHIN LIVING CULTURES

(71) Applicant: New Jersey Institute of Technology, Newark, NJ (US)

(72) Inventors: Roman Serheyevich Voronov, Oklahoma City, OK (US); Quang Long Pham, Saint Louis, MO (US); Nguyen Nhat Anh Tong, Newark, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 662 days.

(21) Appl. No.: 17/072,854

(22) Filed: Oct. 16, 2020

(65) Prior Publication Data

US 2021/0115368 A1    Apr. 22, 2021

Related U.S. Application Data

(60) Provisional application No. 62/916,586, filed on Oct. 17, 2019.

(51) Int. Cl.
*C12M 3/06* (2006.01)
*C12M 1/12* (2006.01)

(52) U.S. Cl.
CPC ............ *C12M 23/16* (2013.01); *C12M 25/02* (2013.01); *C12M 25/14* (2013.01)

(58) Field of Classification Search
CPC ...... C12M 23/16; C12M 25/14; C12M 25/02; C12M 41/00; C12M 41/48; B01L 2400/0638
See application file for complete search history.

(56) References Cited

U.S. PATENT DOCUMENTS 5,863,502 A * 1/1999 Southgate ......... B01L 3/502738
                                                       422/417
6,508,988 B1   1/2003 Van Dam et al.
(Continued)

FOREIGN PATENT DOCUMENTS

AU     2002338373 A1   10/2002
AU     2004304787 A1    7/2005
(Continued)

OTHER PUBLICATIONS

Choi, et al., Microfluidic Scaffolds for Tissue Engineering, Articles, Nature Publishing Gourp, published online: Sep. 30, 2007; doi:10.1038/nmat2022.
(Continued)

*Primary Examiner* — Elizabeth A Robinson
*Assistant Examiner* — Jonathan E Lepage
(74) *Attorney, Agent, or Firm* — McCarter & English, LLP

(57) ABSTRACT

Embodiments of microfluidic systems and methods of manufacturing are described herein, which utilize an automated microfluidic plumbing technology with addressable ports capable of minimally disruptive additive and subtractive (including probing) cell and/or fluid manipulation at any desired location(s) within living cultures. The addressable microfluidic ports may be integrated throughout cell cultures in microfluidic systems for microfluidic tissue scaffolds, in two- or three-dimensional spatial arrangements. The addressable microfluidic ports may be used for controlling
(Continued)

and/or monitoring cell behavior over time at different user-selected locations within cell cultures. Also provided are methods for fabricating such microfluidic devices and microfluidic tissue scaffolds.

19 Claims, 15 Drawing Sheets

(56) References Cited

U.S. PATENT DOCUMENTS

| | | | |
|---|---|---|---|
| 7,097,809 | B2 | 8/2006 | Van Dam et al. |
| 7,670,429 | B2 | 3/2010 | Quake et al. |
| 7,964,139 | B2 | 6/2011 | Liu et al. |
| 8,220,494 | B2 | 7/2012 | Studer et al. |
| 9,205,423 | B2 | 12/2015 | Hansen et al. |
| 9,714,443 | B2 | 7/2017 | Maerkl et al. |
| 10,509,018 | B2 | 12/2019 | Quake et al. |

FOREIGN PATENT DOCUMENTS

| | | | | |
|---|---|---|---|---|
| CA | 2442914 | A1 | 10/2002 | |
| EP | 2596006 | B1 | 5/2013 | |
| JP | 2009001486 | A | 1/2009 | |
| JP | 20100151821 | A | 1/2012 | |
| WO | WO 0167369 | A2 | 9/2001 | |
| WO | WO-03002710 | A2 * | 1/2003 | ............ A61N 1/0543 |
| WO | WO-2018213357 | A1 * | 11/2018 | ......... B01L 3/502715 |

OTHER PUBLICATIONS

Wang et al, A Microfluidic Cell Array with Individually Addressable Culture Chambers, Biosensors and Bioelectronics, 24, 613-617, 2008.

Du, et al, Chapter 7, Microfluidic Systems for Engineering Vascularized Tissue Constructs, Jan. 2009.

Wang et al., Biodegradable Microfluidic Scaffolds for Tissue Engineering from Amino Alcohol-Based Poly(ester amide) Elastomers, Organogenesis 6:4, 212-216, Oct.-Nov.-Dec. 2010.

Huang et al., Microfluidic Hydrogels for Tissue Engineering, IOP Publishing, Biofabrication, 3, 14 pp. 2011.

Leung, et al., A Programmable Droplet-Based Microfluidic Device Applied to Multiparameter Analysis of Single Microbes and Microbial Communities, PNAS, vol. 109, No. 20, 7665-7670, May 15, 2012.

Gao, et al., Digital Microfluidic Programmable Stencil (dMPS) for Protein and Cell Patterning, RSC Advances, 6, 10760-101769, 2016.

Mogosanu, et al., Fabrication of 3-Dimensional Biodegradable Microfluidic Environments for Tissue Engineering Applications, Materials and Design, 89, 1315-1324, 2016.

Zhang et al., Microfluidic Tissue: A Biodegradable Scaffold with Built-in Vasculature for Cardiac Tissue Vascularization and Surgical Vascular Anastomosis, 17$^{th}$ International Conference on Miniaturized Systems for Chemistry and Life Sciences, Oct. 27-31, 2013, Freiburg Germany, three pp. 2019, 2020, 2021.

* cited by examiner

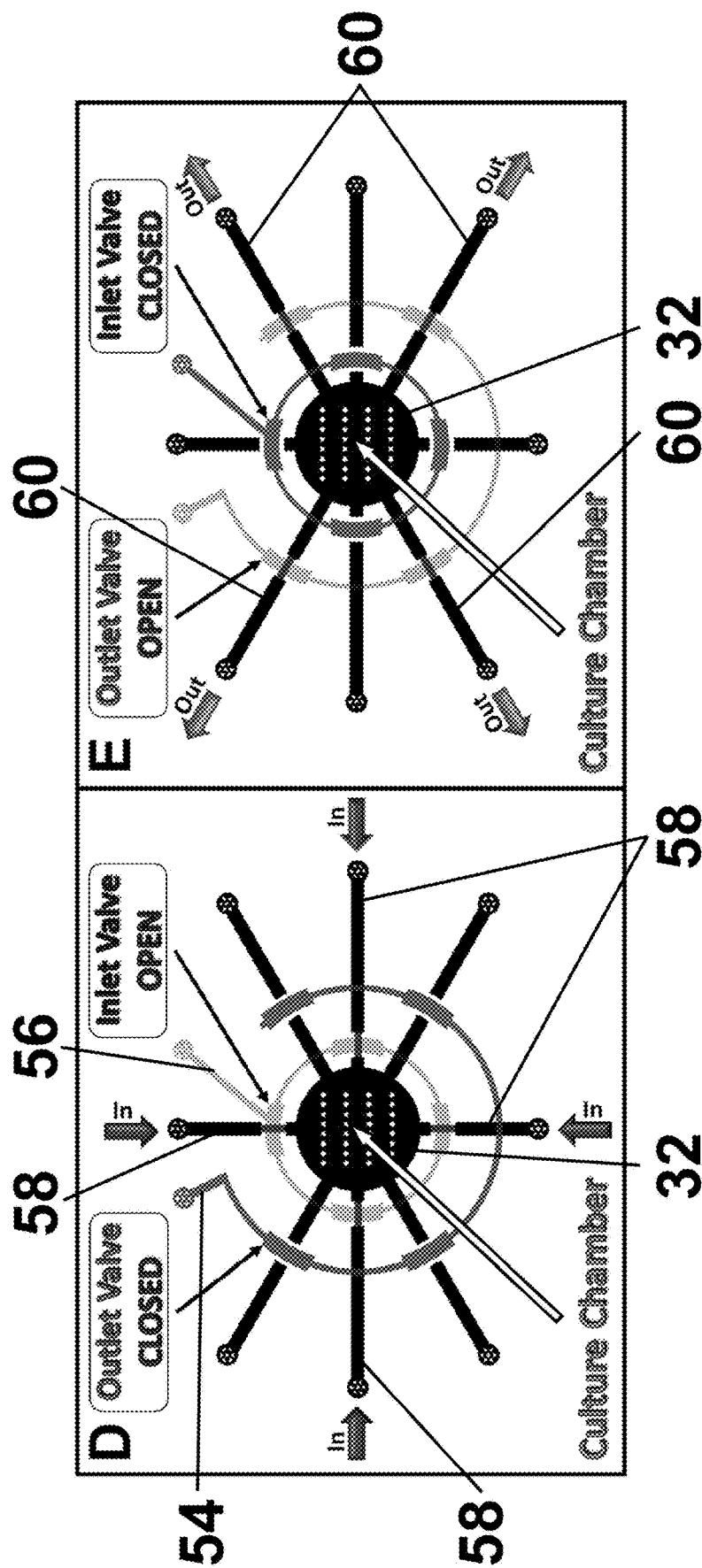

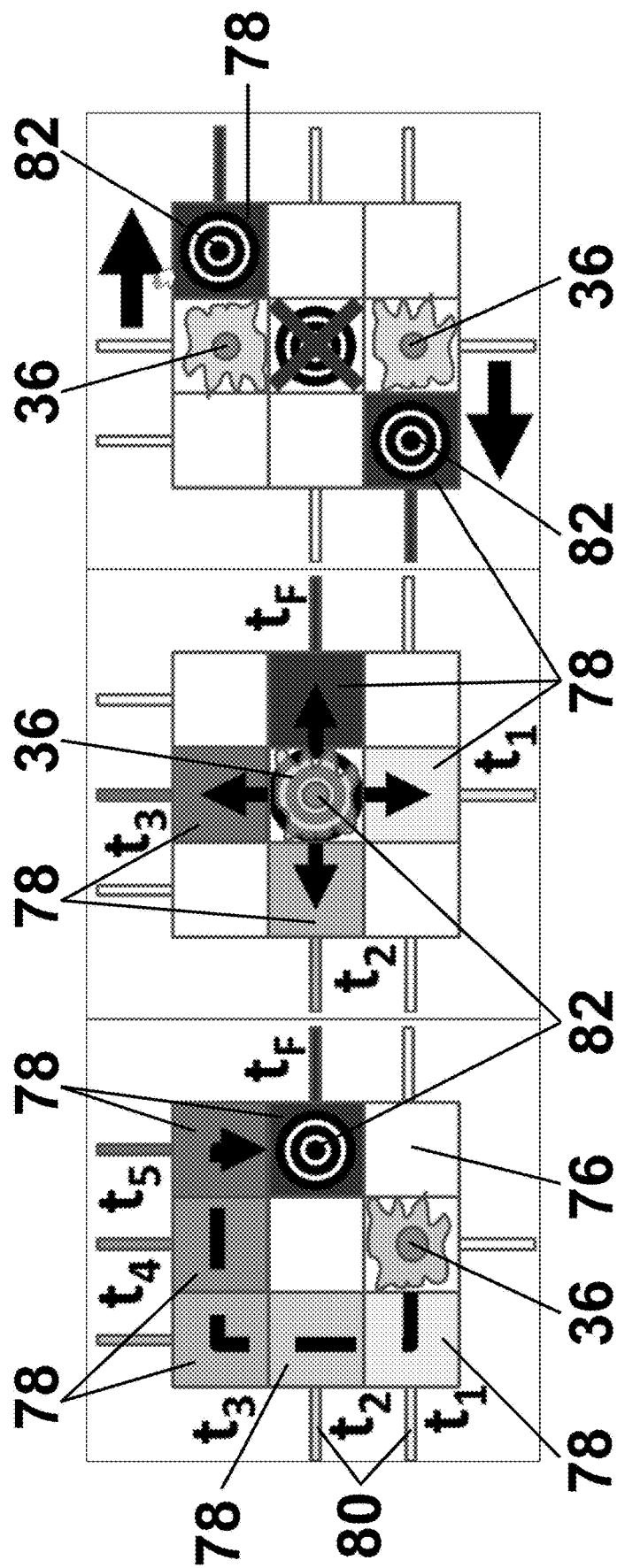

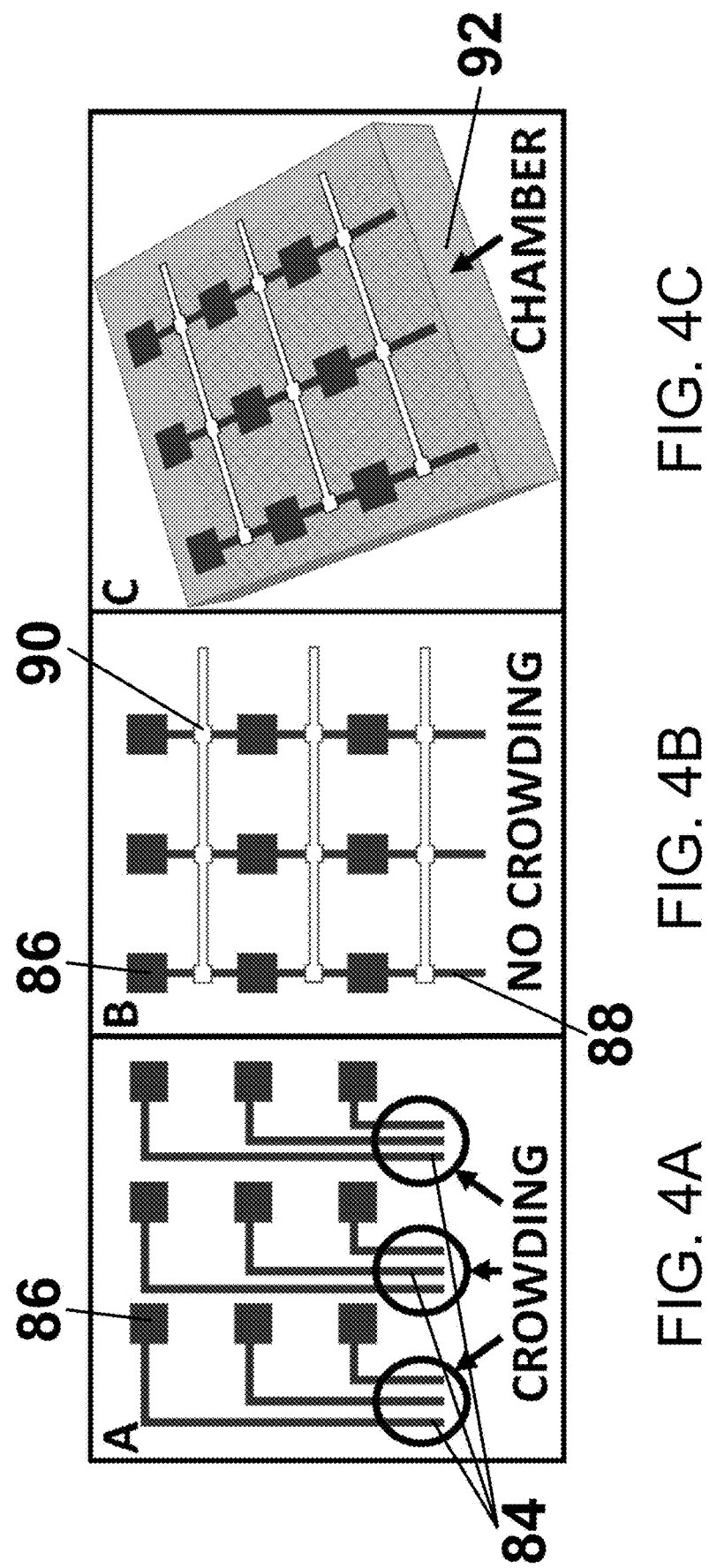

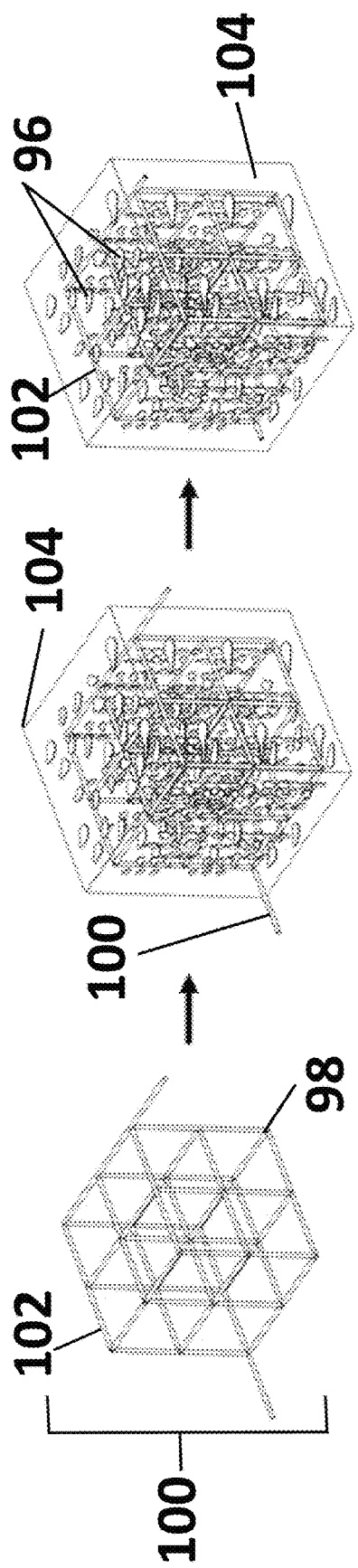
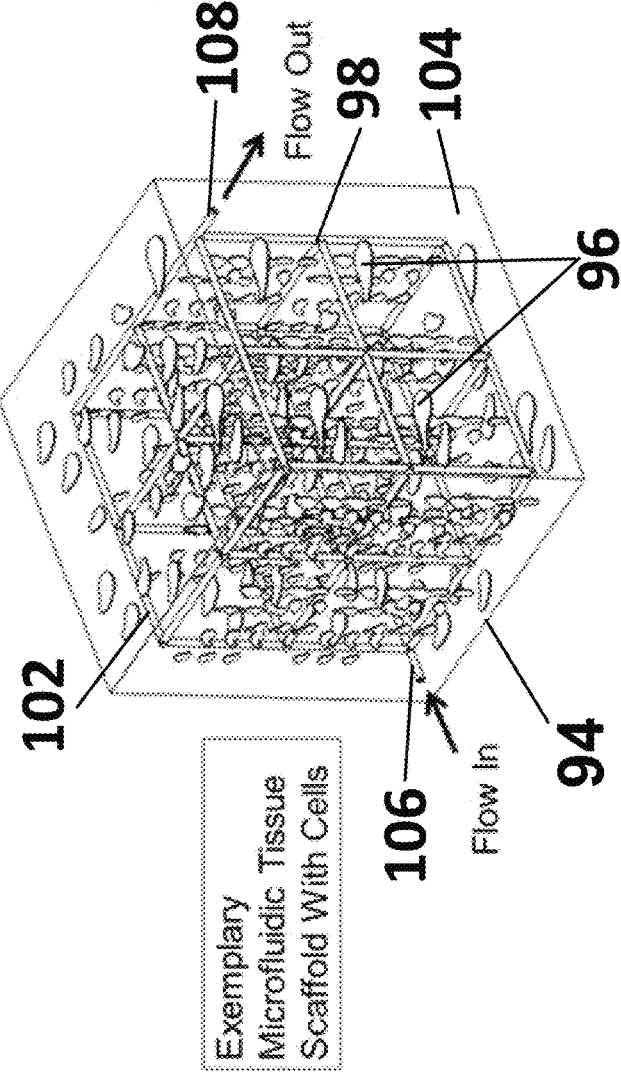
FIG. 5D
FIG. 5C
FIG. 5B
FIG. 5A

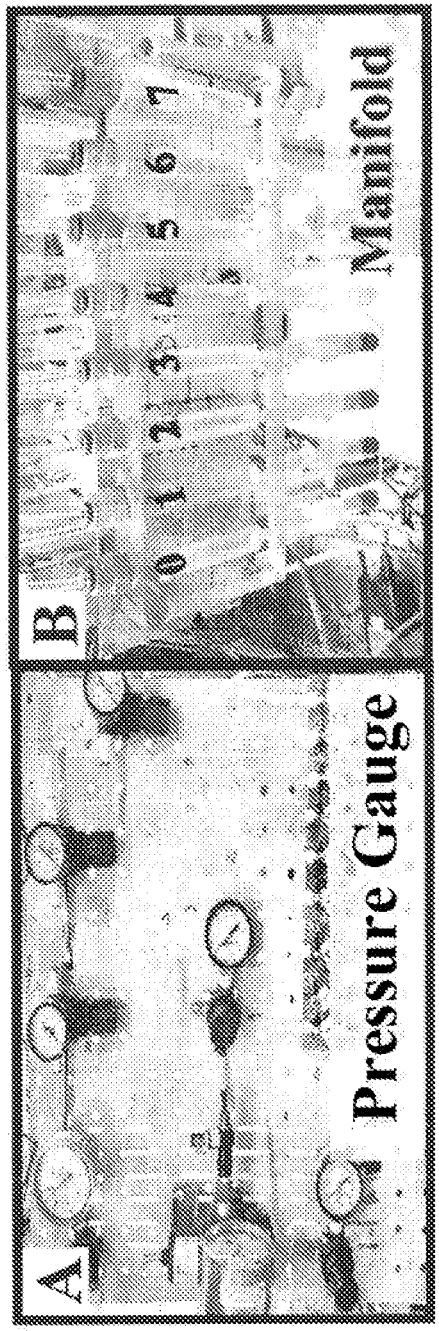
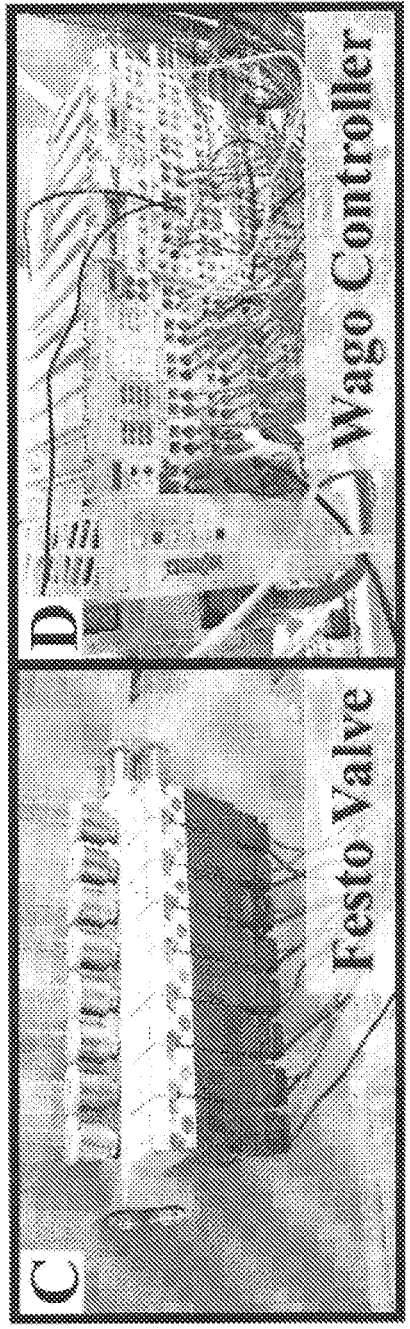
FIG. 6A
FIG. 6B
FIG. 6C
FIG. 6D

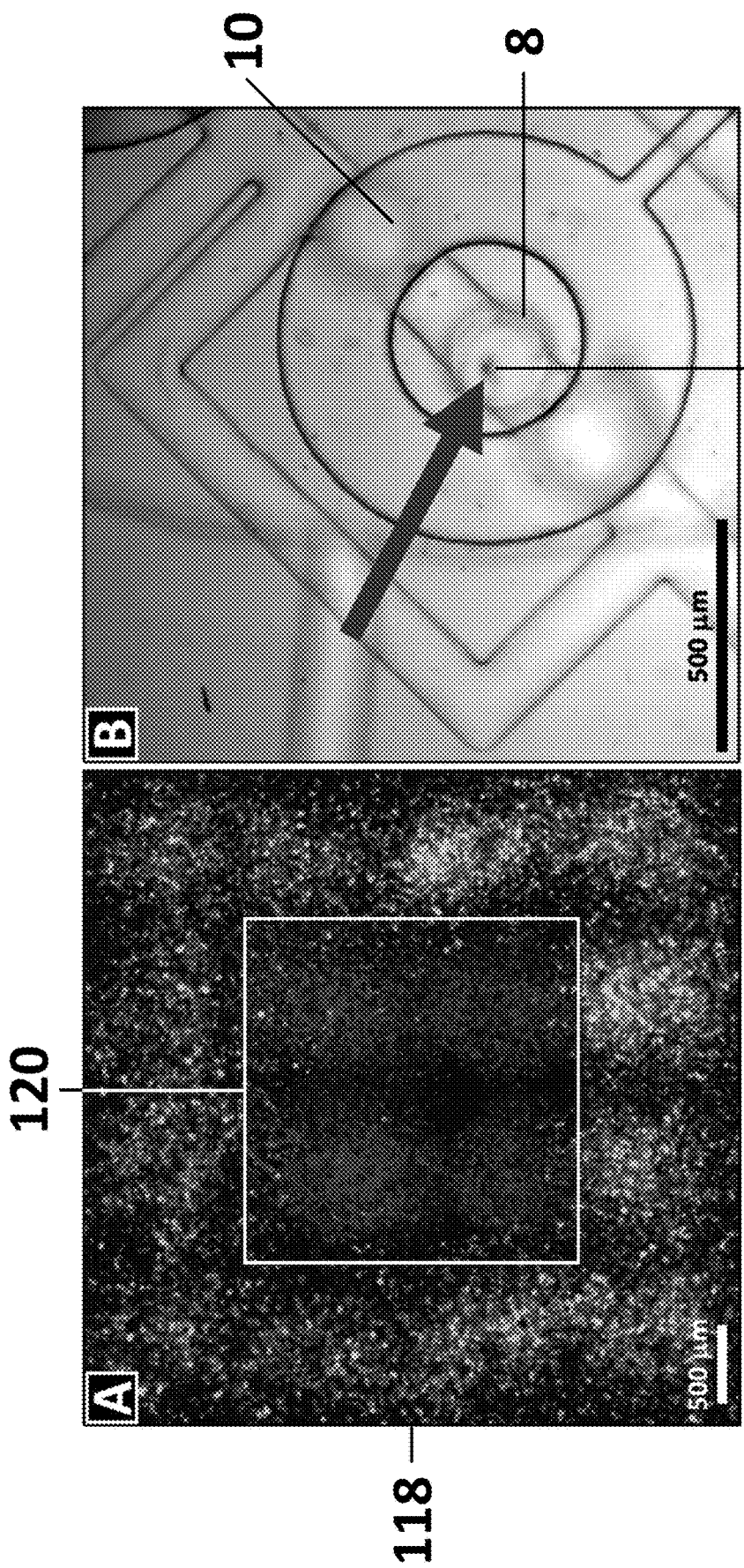

A) Round Profile Micron Features

Positive Photoresist AZ® P4620

Spin coat
HMDS
2500 rpm, 30 secs

Dry (Hot Plate)
150 °C, 5 secs

1st Spin coat
AZ® P4620 - 1400 rpm
FT 14 μm

Soft-bake
90 °C, 10 mins

2nd spin coat
AZ® P4620 - 1400 rpm
FT 28 μm
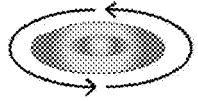

Soft-bake
90 °C, 1 hr

Rehydrate
37 °C, 12 hrs

UV Exposure
2800 mJ/cm²

Develop
AZ® 400k Developer
Immerse, 10-15 mins

Hard Bake
Ramping (4 °C/hr)
65-150 °C, 15 hrs
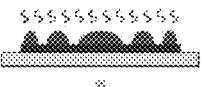

Round Profile
AZ® P4620 mold
Alignment Marks

FIG. 12A

B) Square Profile Micron Features

Negative Photoresist SU-8

Spin coat
HMDS
2500 rpm, 30 secs

Dry (Hot Plate)
150 °C, 5 secs

Spin coat
SU8-2150 - 1250 rpm
FT 550 μm
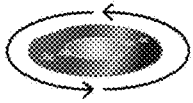

Soft-bake
95 °C, 120 mins

Mask/Wafer Alignment
XY translation Rotation

UV Exposure
600 mJ/cm²

Hard-bake
95 °C, 30 mins

Develop
SU-8 Developer
Immerse, 30 mins

Multilayered Master Mold
Square + Round Profile
SU8 + AZ® P4620 mold

FIG. 12B

AUTOMATED ADDRESSABLE MICROFLUIDIC TECHNOLOGY FOR MINIMALLY DISRUPTIVE MANIPULATION OF CELLS AND FLUIDS WITHIN LIVING CULTURES

BACKGROUND

1. Technical Field

The present disclosure relates to a cell-culturing microfluidic systems utilizing improved microfluidic technology as described herein including improved addressable microfluidic plumbing (e.g., valves, ports, chambers), including two dimensional ("2D") cell culturing devices and three-dimensional ("3D") tissue scaffolds with microfluidic addressable plumbing and cell culture chamber. The cell-culturing device can include addressable microfluidic plumbing for observing and manipulating cells (e.g., controlling cell behavior) in either a 3D addressable microfluidic tissue scaffold or a 2D cell-culturing device. The present disclosure also relates to methods for manufacturing and using the same.

2. Background Art

Tissue and organs in vivo are nourished by blood, which is circulated by the heart through vasculature. In contrast, artificial cell cultures and engineered tissues, including tissue scaffolds that provide structural support for cell attachment and subsequent tissue development, can fail to provide such circulation because they can include passive pores. Passive pores may fail to deliver nourishment to the internal spaces of the engineered tissue (e.g., non-periphery spaces of a tissue scaffold), particularly if they are not connected to a pump (e.g., an ex vivo analogue of the heart As a result, only cells on the periphery of the tissue scaffold may be exposed to nutrients and oxygen in the cell culture media, while the remaining tissue in the center of the tissue scaffold is deprived of such nourishment. This remaining tissue may die as a result of not receiving nutrients and oxygen. As a result, the size of engineered tissue that may be manufactured may be limited; thus, making it difficult to grow clinically-relevant organ-size tissues, or other suitable tissue products.

Moreover, when artificial cell cultures or engineered tissue contain passive pores, access to the cells within them may be impeded. In some cases, all access to the cells can be lost once they are embedded in the tissue scaffold or a cell culture substrate. This may limit the ability for a user (e.g., scientist, physician or other suitable practitioner) to monitor any cellular development by localized chemical sampling within the scaffold. It may also limit the ability for the user to manipulate the cells' behavior and/or development during culturing when delivering signal cues. This lack of access to cells within the interstices of the tissue scaffold or the cell culture substrate may slow down the advancement of tissue engineering data and biological experiments (e.g., knowledge produced from tracking and/or sampling the growth of the cells and tissue that they generate). For example, as a result of the inability to easily study or to affect intra-scaffold cellular activity during culturing, scientists may be compelled to use more basic trial-and-error/black-box approaches (e.g., obtaining single time point bulk-average information from chemical assays on crushed scaffolds). This may hinder the commercialization of tissue engineering technologies because the inability to control cells within the scaffold may lead to low manufacturing resolution, poor product uniformity, and/or high product variability (e.g., varying mechanical properties when manufacturing the same engineered tissue product).

There is currently a need for improvements in microfluidic cell culture technology and tissue scaffolds that contain addressable ports (e.g., openings connected to channels and operated by valves) at points of interest where cell and/or chemical delivery and/or sampling may be performed. Likewise, there is a need for 3D microfluidic platforms with access ports that are addressable at specific locations within the 3D space of the platform; and, specifically, 3D microfluidic tissue scaffolds and cell cultures having 3D microfluidic addressable access ports that allow for targeting precise XYZ locations within a tissue scaffold or cell culture.

SUMMARY

Prior art methods to culture cells in three dimensions depend on a cell-seedable biomaterial to define the global structure of the culture and the microenvironment of the cells. Previous efforts to tailor these scaffolds have focused on the chemical and mechanical properties of the biomaterial itself. The present application provides improved microfluidic systems and microfluidic cell culturing scaffolds that may extend their use into three dimensions. The present application also provides improved microfluidic cell culturing scaffolds that may allow for improved cellular control within the interstices of a 3D microfluidic platform (e.g., 3D tissue scaffold).

The application presents new solutions using addressable microfluidic plumbing (e.g., channels, valves, ports, chambers, etc.) to allow improved control of the distribution of soluble chemicals and cells within the 3D microfluidic platform (e.g., 3D tissue scaffold) with convective mass transfer via microfluidic networks embedded directly within the cell-seeded biomaterial. The present application may provide improved cell cultures that can comprise addressable microfluidic plumbing within cell cultures and/or tissue scaffolds. The improved cell cultures can comprise: one or more tissue scaffolds; active microfluidic pores for sampling (or removing) and delivery of chemicals (e.g., nutrients, oxygen and/or signals) and/or cells throughout the one or more tissue scaffolds; materials for improved microscopic observation of cellular growth and development; and "addressable" access ports (openings connected to channels and operated by controllable valves) designed for localized chemical delivery and/or sampling. Improved cell and chemical delivery and/or sampling may yield improved cellular control and tissue patterning, and may also permit improved monitoring and altering of culture or tissue development.

Conventional microfluidic platform designs, including tissue scaffold designs, do not allow for addressable delivery or sampling of cells and fluids at different locations within their void spaces (e.g., microfluidic pores or cell culturing chambers and compartments, etc.) as set forth herein. The present application provides microfluidic systems having addressable ports at points of interest selected by a user (e.g., scientist, physician, or other suitable practitioner). In an exemplary embodiment, the microfluidic systems can be used in both 2D and 3D cell and/or tissue cultures. Some embodiments of a microfluidic platform may comprise a 2D cell culture or a 3D microfluidic tissue scaffold. The microfluidic platform may comprise addressable ports. The addressable ports may be used for the delivery and/or sampling of chemicals and/or cells in the 2D microfluidic cell culturing device, or 3D tissue culturing scaffold, or any other suitable 3D microfluidic platforms. In an exemplary embodiment, the addressable ports may be openings connected to flow channels and operated by microfluidic addressable valves. In some embodiments, the design of the addressable ports may be selected based on the opening size and depth, including but not limited to: the type of material used by the addressable microfluidic platform (e.g., biomaterial used for a 2D cell culturing device or 3D microfluidic tissue scaffolds); the type of microfabrication method used to manufacture the addressable microfluidic platform (e.g., 3D printing, 3D bioprinting, stereolithography, soft lithography, replica molding, gel casting a sacrificial template, etc.); and the type of architectural design of the addressable microfluidic device.

Also provided are methods of manufacturing addressable microfluidic systems, comprising a 2D cell culturing device or 3D microfluidic tissue scaffold comprising microfluidic addressable access ports (openings connected to channels and operated by controllable valves). In an exemplary embodiment, the addressable ports may be manufactured from polydimethylsiloxane ("PDMS"), or any other suitable (e.g., biocompatible, biodegradable) material. In an example, the addressable ports may be manufactured for use in cell behavior control in a culture or in a tissue culturing scaffold.

Automated addressable microfluidic plumbing (i.e., a combination of valves, ports, channels, chambers, etc.) technology used in the systems described herein enables users to perform minimally disruptive additive and/or subtractive (including probing) manipulation of cells and chemicals within living 2D and 3D cell cultures. Applications of embodiments of this technology as described herein include, but are not limited to, automated cell culturing platforms and engineered tissue scaffolds.

The microfluidic plumbing technology described herein overcome size limitations associated with prior art systems (such as tissue or cell culture necrosis) currently limiting the growing of thick 3D cell cultures and tissues in those prior art systems. Embodiments of the invention describe herein overcome these size limitations by, for example and without limitation, supplying oxygen and nutrients to cells located in deep portions of the cultures and tissue scaffolds via the microfluidic channels and ports. These cells located in deep, and more difficult-to-access portions of cell cultures and tissues were not readily accessible using prior art systems.

The microfluidic plumbing technology as described herein can also eliminate the reliance on sacrificial analysis by enabling real-time minimally disruptive localized cell and fluid probing from any location within a 2D or 3D culture or tissue scaffold and at any time during the culturing process.

Additionally, the microfluidic plumbing technology as described herein can reduce reliance on human labor by automating the cell and artificial tissue culturing processes.

The microfluidic plumbing technology described herein can also facilitate the adoption of new biological products from lab to market by automating the cell and artificial tissue culturing protocols. For example, a computer could execute automated culturing protocol programs that seed and control cell culturing using microfluidic systems as described herein, which would eliminate the need to train new culturing procedures to human staff for each new biological product that needs to be cultured on site (e.g., at a hospital, company, research facility, etc.). This aspect of the present invention allows for quicker and less error prone rollout of new biological products that are created via cell culturing as a result.

Further, the microfluidic plumbing technology described herein improves over prior art systems by minimizing product variability by enabling computerized orchestration over the cell actions within a 2D and/or 3D cell culture and tissue scaffold environments. In other words, specialized software specifically designed and configured to control the microfluidic systems described herein can be uniquely implemented via specially configured computers to minimize deviations from the set point in a closed loop manner, based on real-time culture analysis via cell and fluid probing; as well as based on microscopy feedback.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

FIGS. 1D-1E illustrate a zoomed out top XY view of an exemplary schematic of the culture chamber with the circular control valves that can allow and/or prevent fluids from entering and/or leaving the chamber via the surrounding inlet and outlet channels, according to aspects of the present disclosure.

FIGS. 3A-3C are exemplary use cases of the exemplary addressable microfluidic valves of FIG. 1B for controlling cell migration, according to aspects of the present disclosure.

FIG. 4A illustrates an embodiment of an addressable microfluidic plumbing system with inefficient X*Y scaling and the resolution limitations due to crowding of the supply channels, according to aspects of the present disclosure.

FIG. 4B illustrates an embodiment of an addressable microfluidic plumbing system with efficient (X+Y) scaling and the resolution is not limited by the crowding, according to aspects of the present disclosure.

FIG. 4C illustrates how an exemplary addressable microfluidic plumbing is connected to a single culturing chamber, according to aspects of the present disclosure.

FIGS. 5A-5D illustrate an exemplary 3D addressable microfluidic tissue scaffold with cells, as well as the manufacturing steps for fabricating it using a sacrificial template gel casting method, according to aspects of the present disclosure.

FIGS. 6A-6D illustrates exemplary hardware components of a programmable pneumatic pumping system for operation and automated control of multi-layers addressable microfluidic cell culturing platforms, according to aspects of the present disclosure.

FIGS. 7A-7C illustrates an exemplary graphical user interface ("GUI") for controlling an exemplary pumping system via a proportional-integral-derivative ("PID") controller, according to aspects of the present disclosure.

FIGS. 9A-9B illustrates an exemplary minimally-disruptive additive cell manipulations within the culture chamber of the device, according to aspects of the present disclosure showing A) mesenchymal stem cells (MSCs) (white) seeded in a square shape that surrounds the NIH/3T3 cells (gray) deposited in its center of the culture chamber; and B) an exemplary demonstration of single cell manipulation precision.

FIG. 11A illustrates a confluent layer of cells prior to the manipulation. FIG. 11B illustrates disc-shaped patterns (marked with white circles) removed from the confluent layer via the cell subtraction.

FIGS. 12A-12B is a schematic showing an exemplary step-by-step fabrication process of a multi-layered master mold, composed of two different heights/profiles (round and square) of micron-sized features on a 4-in silicon wafer, according to aspects of the present disclosure.

DETAILED DESCRIPTION OF CERTAIN EMBODIMENTS

Figures 1A, 1B:
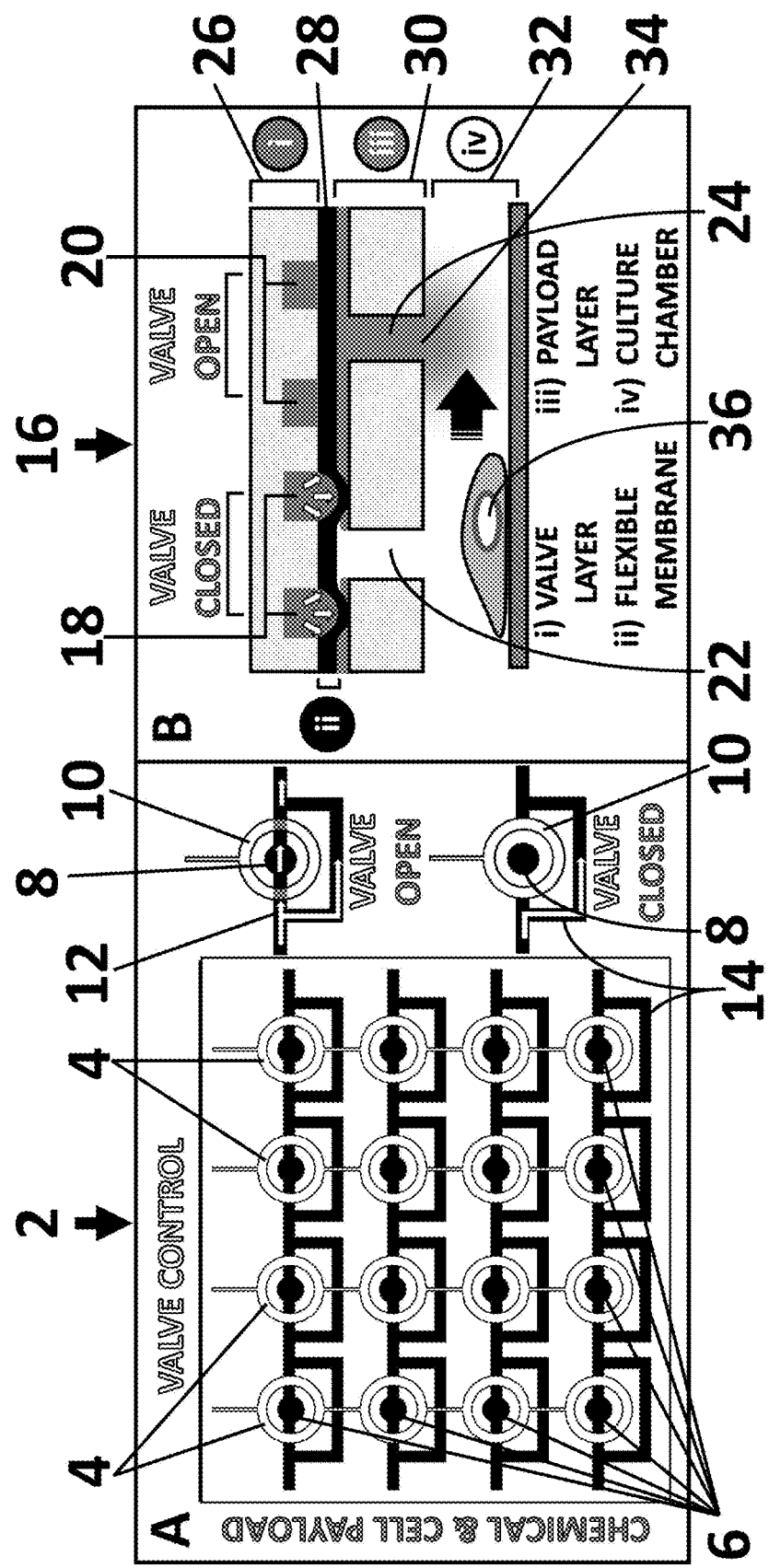
FIG. 1A is top XY view of an exemplary addressable microfluidic plumbing system comprised of a 4×4 matrix of the addressable ports and 0-shaped microfluidic addressable valves, according to aspects of the present disclosure.
FIG. 1B is a Z cross-sectional view of an exemplary addressable microfluidic plumbing system, according to aspects of the present disclosure.

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

As used herein "tissue scaffold" may refer to any porous or highly porous scaffold bio-compatible material, which may act as a template for tissue regeneration or cell culturing experiments, to guide the growth of new tissue or the cell distribution in the 3D culture.

As used herein "microfluidics" may refer to any device or devices that use micro-sized channels. connected to a pumping source, for delivery or sampling of fluids within artificial biological environments. Such devices may be used for cell culture experiments mimicking tissue environments, biomanufacturing, disease modeling, toxicity testing, and the like.

As used herein, the term "compartment" can refer to a physically delineated space, such as a space between walls and/or housing (e.g., a channel through a membrane), or it can refer to an area or region in space (e.g., a position in a cell culture). For example, a compartment may refer to a region in space positioned within a three-dimensional microfluidic scaffold structure or a position between or proximal to valves. In some instances, the terms "port" and "compartment" can be used interchangeably because these terms can refer to an area in space relative to the position of a valve, wherein one of skill in the art (in view of the present disclosure) would understand how to arrange and manipulate valves and microfluidic plumbing to deliver a payload to one or more desired compartments depending upon the particular configuration of the microfluidic system.

One of skill in the art would immediately envisage, in view of the present disclosure, the meaning and scope of a compartment and ports as used herein.

Various aspects of the present disclosure relate to microfluidic systems, including cell cultures and 3D microfluidic tissue scaffolds, that further include addressable plumbing (i.e., channels, valves, ports, chambers, and the like). For example, an exemplary 3D addressable system according to aspects of the present disclosure may comprise a combination of channels, valves, ports, and/or chambers. In some embodiments, chambers without a bottom floor wall may be referred to as a port. In an exemplary embodiment, a microfluidic system or microfluidic scaffold may comprise a plumbing system comprising addressable microfluidic valves. A plumbing system may also comprise a pumping system. The combination of pumping system and valves (both on-chip and off-chip) may be used to deliver or draw fluid (e.g., cell culture media containing a biological agonist) and/or cells to/from each address (e.g., location of interest in an array of addressable chambers, ports, valves, etc.) by actuating the corresponding address (i.e., port). In some embodiments, the actuation may be achieved via an on-chip valve, or valves that may either guide the fluid's (which could be carrying a chemical and/or cells payload) path to or from a port, or may route the payload to bypass the port. In some embodiments, the on-chip valves may comprise on-chip microfluidic valves that are driven by off-chip (i.e. external) solenoid valves.

According to aspects of the present disclosure, the disclosed addressable microfluidic plumbing systems may be configured to enable targeted fluid and/or cell delivery and/or removal (including collecting for sampling) at targets (i.e., precise locations) within a tissue scaffold or a cell culturing device, and with a high spatial resolution. Some exemplary microfluidic system embodiments disclosed herein may include addressable ports at points of interest (i.e., select points where either chemical delivery and/or sampling may be performed in a microfluidic scaffold or device).

Addressable microfluidic plumbing systems comprising valves, chambers, ports, and/or supply channels may permit a microfluidic cell culturing device (e.g., 3D microfluidic tissue scaffold) to monitor and/or control cell behavior at a targeted locations within the device, or in a tissue scaffold, for the purposes of, but not limited to: regenerative medicine, tissue engineering, drug discovery, wound assays and biomedical devices.

In regenerative medicine and other applications, the microfluidic addressable valves disclosed herein may assist in tissue patterning by selective delivery of cell differentiation factors and other agonists to different parts of a tissue scaffold. The disclosed addressable microfluidic ports may also manipulate cell behavior via localized chemo-signal delivery. The microfluidic valves may also be used for non-invasive cell and tissue development monitoring by performing localized chemical probing (e.g., for ex-situ sacrificial assays) within the tissue scaffold during culturing, and without sacrificing the sample or disrupting the experiment. Lastly, the microfluidic valves may be useful in adaptive culturing control with real-time feedback (e.g adjusting culturing conditions based of observed cell behavior and/or tissue development) by combining cell control with monitoring.

According to aspects of the present disclosure, microfluidic addressable plumbing (e.g., ports, chambers, flexible valves, etc.) as disclosed herein may also be used for cell development during drug discovery. In other words, a response, or responses, to drugs may be monitored in real-time by delivering different doses of drugs to various locations within a colony of cultured cells or in a living tissue.

Biomedical devices can incorporate the disclosed microfluidic addressable plumbing to operate as an organ-on-a-chip device, and may be used for drug development, diseases modeling, and/or personalized medicine—where spatial chemical delivery or sampling may be necessary.

Addressable microfluidic plumbing as described herein can be implanted in-vivo and may be used to monitor responses to biomaterial implants or drug interactions occurring within the body.

With initial reference to FIG. 1A, an exemplary microfluidic plumbing system 2 with addressable ports is shown. In order to modulate localized cell behavior in an addressable microfluidic platform (e.g., microfluidic tissue scaffold), microfluidic addressable plumbing may be used to individually target an "address" (i.e., a spatial location with a corresponding microfluidic port operated by a microfluidic valve), if necessary. FIG. 1A illustrates an exemplary port-valve configuration 4. The configuration of FIG. 1A illustrates a 4×4 matrix of addressable ports 6. The 4×4 size was chosen as a demonstration example, while in other embodiments the matrix can be of any 2D or 3D size. The port 8 may comprise a cylinder-shaped opening that may be surrounded by an "O-shaped" pneumatic valve 10. In some embodiments, pneumatic valve 10 may have a "C-shape" (not shown since operation is similar to the O-shaped valve 10). Pneumatic valve 10 may be selectively opened or closed (e.g., addressable) to control the flow of a fluid carrying chemical agonists, cells, or other suitable payloads used in cell culture and tissue scaffold development. When valve 10 is "open" a corresponding port 8 may be supplied with an appropriate payload via micro-channels 12. When valve 10 is "closed", the payload may be re-routed around port 8 via a bypass 14, as shown. A port, which may be referred to as an address or targeted location in certain embodiments, may be considered "active" when valve 10 is open, and bypassed or "inactive", when valve 10 is closed. A port may also refer to an area or point in space in a microfluidic system described herein, where that point or area is a place that can have payloads directed to it via the aspects described herein.

With initial reference to FIG. 1B, a cross-section of an exemplary addressable microfluidic plumbing system 16, according to aspects of the present application, is shown. As alluded to above, the exemplary microfluidic addressable plumbing system 16 may comprise a valve (in a "closed" 18 and/or "open" 20 positions), and port (in an inactive 22 or in active 24 states), according to aspects of the present disclosure. The cross section of a single 2D array of microfluidic ports was chosen as a demonstrative example, while in other embodiments the plumbing may consist of multiple such arrays stacked to form a 3D structure.

As used herein, the meaning ascribed to the terms 2D and 3D would be immediately envisaged by the skilled artisan when viewing the disclosure and claims contained herein. A 2D structure may refer to an embodiment such as that shown in FIG. 1A, wherein such an embodiment may contain valves and a microfluidic plumbing system arranged to direct payloads in the X-Y dimensions to ports. A 3D structure may refer to a microfluidic device that employs a microfluidic scaffold, which further allow for control of payload delivery in three dimensions, e.g., X-Y-Z.

Addressable microfluidic plumbing configurations 2 and 16 may be fabricated using soft lithography, or any other suitable microfabrication method used to make microfluidics devices, for example, 3D printing (e.g. direct extrusion and/or stereolithography, or replica molding, or gel casting a 3D printed sacrificial template, etc.). In an exemplary embodiment, and as shown in FIG. 1B, an addressable microfluidic plumbing configuration 16 may comprise four layers: a valve layer 26, a thin flexible membrane 28, a chemical-and-cell-payload flow layer 30, and a cell culture chamber or compartment 32. It should be understood that in some embodiments, the addressable microfluidic plumbing system 16 may include fewer or more than four layers. Valve layer 26 may comprise one or more addressable valves (e.g., microfluidic addressable valves 18 and 20). in some embodiments of the present disclosure, a pumping system may be used to pump fluid into the addressable microfluidic plumbing system 16. Fluids may be delivered into, plumbing system 16 from a pressurized source. The pressure may be reversed to draw fluid from plumbing system 16. For example, the pressure in the pumping system may be used to deliver fluids containing biological cell agonists into a tissue scaffold. In some other examples, however, the pressure may be reversed to draw fluid from the tissue scaffold for ex-situ analysis. Chemical-and-cell-payload flow layer 30 may comprise a suitable fluid (e.g. media with cell agonist chemicals or cell suspension, or the like). It can be appreciated that chemical-and-cell-payload flow layer 30 may be a flow layer for any chemical that can be delivered and/or sampled using the addressable microfluidic plumbing system 16. Chemoattractant is an example of one type of chemical that may be employed by the addressable microfluidic plumbing system 16.

In some embodiments, chemical-and-cell-payload flow layer comprise flow channels 12, bypasses 14, and/or addressable ports 22 and 24. As shown in FIG. 1B is an exemplary embodiment of the addressable microfluidic plumbing system 16, chemical-and-cell-payload flow layer 30 comprises an addressable ports 22 and 24, which includes openings (e.g., cylinder-shaped chambers 22 and 24 without any "floor"), which may allow the opening 22 and/or 24 to act as a fluid-release or fluid-sampling "ports". During the operation of the addressable microfluidic plumbing system 16, when valve 18 is closed, the fluid may be blocked from entering the adjacent port 22 of the chemical-and-cellpayload flow layer 30. When valve 20 is opened, the fluid 34 (labeled in gray color in FIG. 1B) may be permitted to release from the chemical-and-cell-payload flow layer 30 to cell culture chamber 32 via the opening of the addressable port 24, as shown in FIG. 1B. FIG. 1B illustrates how, during operation of the addressable microfluidic plumbing system 16, a cell 36 neighboring an active microfluidic port 24 is attracted towards it, due to the chemical (e.g., nutrients, chemoattractant, etc.) payload being flown through the micro channels 12 (FIG. 1A) of the chemical-and-cell-payload flow layer 30, and then released into the culture chamber 32 at the active microfluidic port 24 location. At the same t me, it is shown that the inactive port 22 directly above the cell 36 does not affect its behavior, since no chemical payload is being delivered through this address. The localized release of the fluid carrying a chemical agonist payload 34 (labeled in gray color in FIG. 1B) may attract cell 36 towards a desired location within the addressable microfluidic plumbing system 16 (e.g., target location(s) within a tissue culture scaffold to control cellular development and/or growth).

Figure 1C:
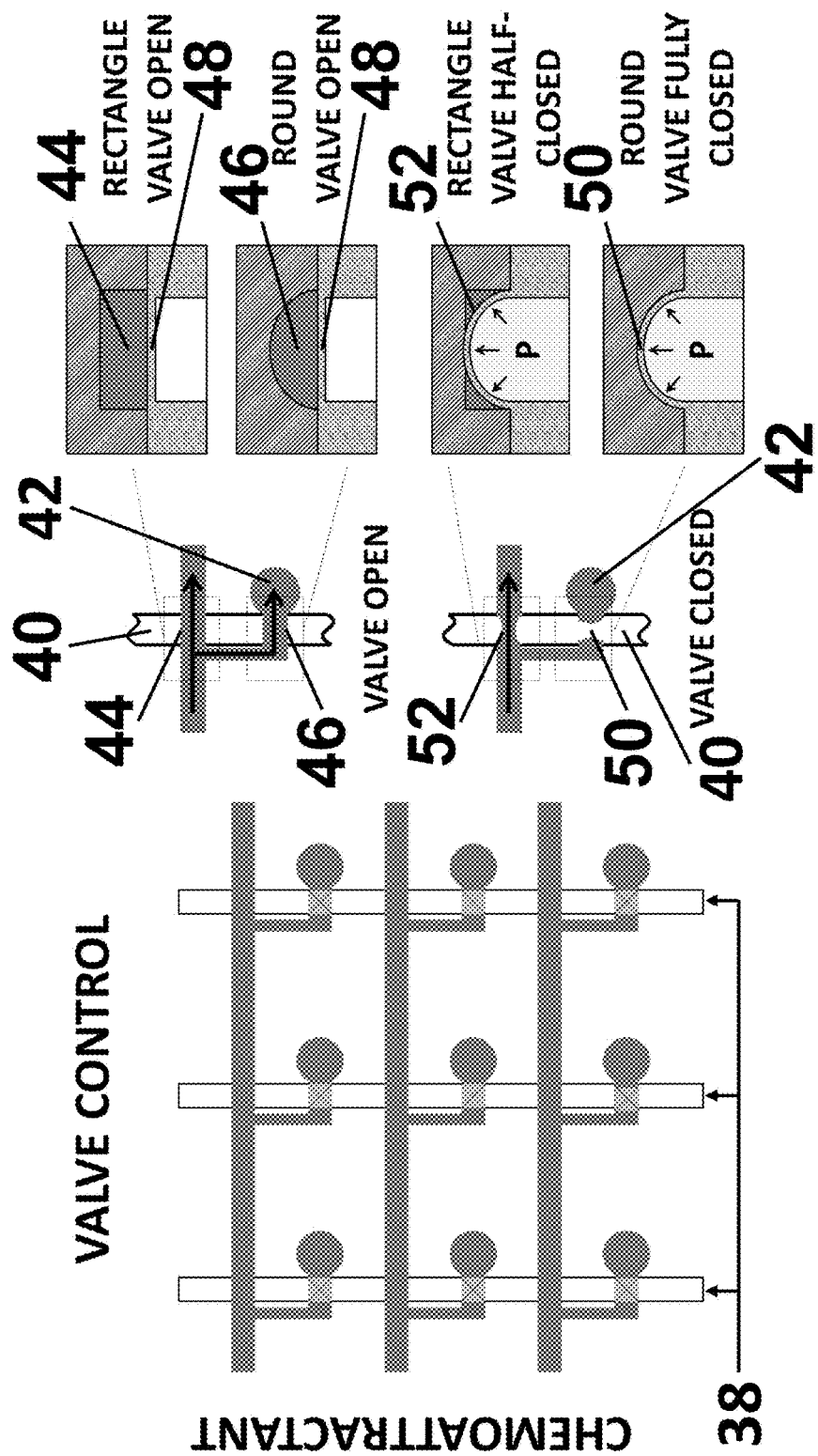
FIG. 1C illustrates an exemplary alternative (I-shaped) control valve design for an exemplary addressable microfluidic plumbing system according to aspects of the present disclosure.

In an embodiment, addressable valves 4 of a microfluidic plumbing with addressable ports design 2 may comprise an "O-shaped" profile 10 or an "I-shaped" profile 38. FIG. 1C shows a layout of an exemplary addressable system using, straight ("I-shaped") valves 40 to control the chemical-and-cell-payload delivery to an addressable port 42. The actuation of these addressable valves is also based on a pneumatic mechanism. The right side of FIG. 1C shows an exemplary mechanism of operation of the I-shaped microfluidic pneumatic valves 40. The flow channels 44 and 46 above the flexible membrane 48 may be rectangular (i.e., sieve valve) 44 or round in shape 46. A round valve may include a round profile, which may be fully closed 50 using a relatively small amount of pressure. The round valve pressure may use a pressure range between about 10 psi to about 25 psi, about 10 to about 15 psi, about 12 to about 14 psi, about 13 psi, about 13.4 psi, and ranges therebetween. Conversely, the rectangular valve 44 may remain in a "half-closed" state 52, when the same pressure is applied. This may allow fluid to be transferred through the flow channel 44 to the next port downstream. Thus, the two types of channel profile shapes are utilized in different parts of the plumbing network in order to achieve the addressability of the microfluidic ports: rectangular profiles for the main flow channel 44 and round profiles for peripheral delivery channels 46 that feed the microfluidic port 42. When the I-shaped valve 40 is deflated, the cell-and-chemical payload is carried through both channels 44 and 42. However, the payload's path to the port 42 may be blocked off by the full closure 50 of the main flow channel 46 (which is achieved by the channel's rounded profile).

With reference to FIG. 1B, Thin flexible membrane 28 may be formed from a flexible and elastic substrate or other suitable flexible and elastic material. With continuing reference to FIG. 1B. during operation, and when addressable valve 18 is in a "closed" position, flexible membrane 28 below the addressable valve 18 may be pressurized and expanded to block the chemical-and-cell-payload layer 30 and isolate the addressable port 22; thus, the chemical or cell suspension may be required to travel through a bypass channel, as described earlier in this disclosure. Therefore, in an exemplary embodiment, valves 18 and 20 may be actuated to permit, or block, the flow of chemical and/or cell payload thorough the addressed port 24 within the addressable microfluidic plumbing system 16.

In an embodiment, a cell culture chamber may be disposed below chemical-and-cell-payload flow layer 30 and addressable ports 22 and 24. In some embodiments, micron sized posts (not identified) inside the culture chamber 32 (e.g. the locations where the microfluidic valves 18 and 20 are) may be introduced as load-bearing posts and prevent the chemical-and-cell-payload flow layer 30 and addressable ports 22 and 24 from collapsing.

With continuing reference to FIG. 1, in some aspects of the present disclosure, the addressable microfluidic plumbing system 16 may include automation. For example, a computer processor (not identified) may be used to detect and/or track cells in real time and non-invasively. In an example, the computer processor may include a microscope, a camera, and corresponding software. In an exemplary embodiment, a controller algorithm (e.g., proportional-integral-derivative, machine learning-based, or the like) may then be used to receive information about the observed locations of the cells, and modulate addressable valves 18 and 20 and 40, which may also comprise ports 20, 24, and 42, using pumping automation in order to guide the cells along a prescribed path. I n other embodiments, and according to aspects of the present disclosure, valves disclosed herein may be automated for controlling a large number of addresses (e.g., addressable valves, ports, and the like). For example, automation may be performed via a programmable logic controller that may actuate off-chip solenoid valves. In some embodiments, computer software may be used for automation when controlling a large number of addressable valves, ports, and the like. The computer software utilized for controlling the microfluidic systems described herein will be specially configured to control the features of these systems, including but not limited to, the sequence of opening and closing control valves, flow rates of payload and/or cell cultures, the length of time payloads and/or cell cultures flow through the system such as through fluid flow channels, and control ling the specific location to deliver payloads and/or cell cultures. The ordinarily skilled artisan would immediately envisage how to configure the software to achieve these objectives and the other objectives described herein when viewed in light of the disclosure.

With continuing reference to FIG. 1B, cell culture chamber 32 may be sized, shaped, and/or designed to permit the growth and behavior (e.g. mobility) of one or more cells 36 inside the cell culture chamber 32 in response to biological cell agonists delivered through addressable ports 22 or 24. This function may allow a user to monitor and/or control the one or more cells behavior at any targeted locations within the addressable microfluidic plumbing system 16. Monitoring and/or controlling cell migration within a microfluidic plumbing system can be used for the purposes of, but not limited to: regenerative medicine delivery, tissue engineering, drug discovery, biological assays (e.g., wound healing), toxicity testing, manufacturing of biological molecules, and biomedical devices.

Additionally, in an exemplary embodiment, the culture chamber 32 in FIG. 1B is supplemented with side channels for: replenishing the media, uniform seeding of the cells and flushing of the chamber. FIGS. 1D-1E show zoomed out top views of the cell culture chamber 32 and two surround ng circular valves 54 and 56 that are introduced in order to control the flow "in" to (see FIG. 1D), and "out" of (see FIG. 1E), the chamber via the side channels 58 and 60, respectively. The mechanism of the circular valves 54 and 56 is the same as the "O-shaped" control valves 10 for the chemical-and-cell-payload flow layer 30 in FIGS. 1A-1B. Unlike in FIG. 1A, there are no bypass channels 14 in this layer.

Instead, the circular valves 54 and 56 were designed to fully block the flow in or out of the cell culture chamber 32 if necessary. Like the automated operation of the addressable ports, the circular control valves (individually, or in groups) can be opened or closed on demand using the control software. This allows the device to replenish the old media in the culture chamber 32 without the need to actuate the addressable ports 22 or 24 (FIG. 1B). Specifically, FIG. 1D shows that the fluid and cells can be added to the cell culture chamber 32 through the 4 inlet channels 58 when the inlet control valve 56 is "open" and the outlet control valve 54 is "closed". Moreover, fresh media can be delivered to the culture chamber through the inlets 58 at fixed intervals (e.g. every 5 hours). Likewise, undesired media and cells can be flushed out of the culture chamber 32 through the outlets 60 showed in FIG. 1E when the inlet control valve 56 is "closed" and the outlet control valve 54 is "open". Additionally, both control valves can be closed at the same time in order to prevent any fluid currents inside of the culture chamber. In some embodiments, this is extremely important at the seeding stage, when the cells require a static condition in order to form focal adhesions with the substrate. Lastly, it is understood that in other embodiments, the number of the inlet control valves 56, outlet control valves 54, inlets 58, and outlets 60 may scale with the size of the addressable port array.

Figure 2:
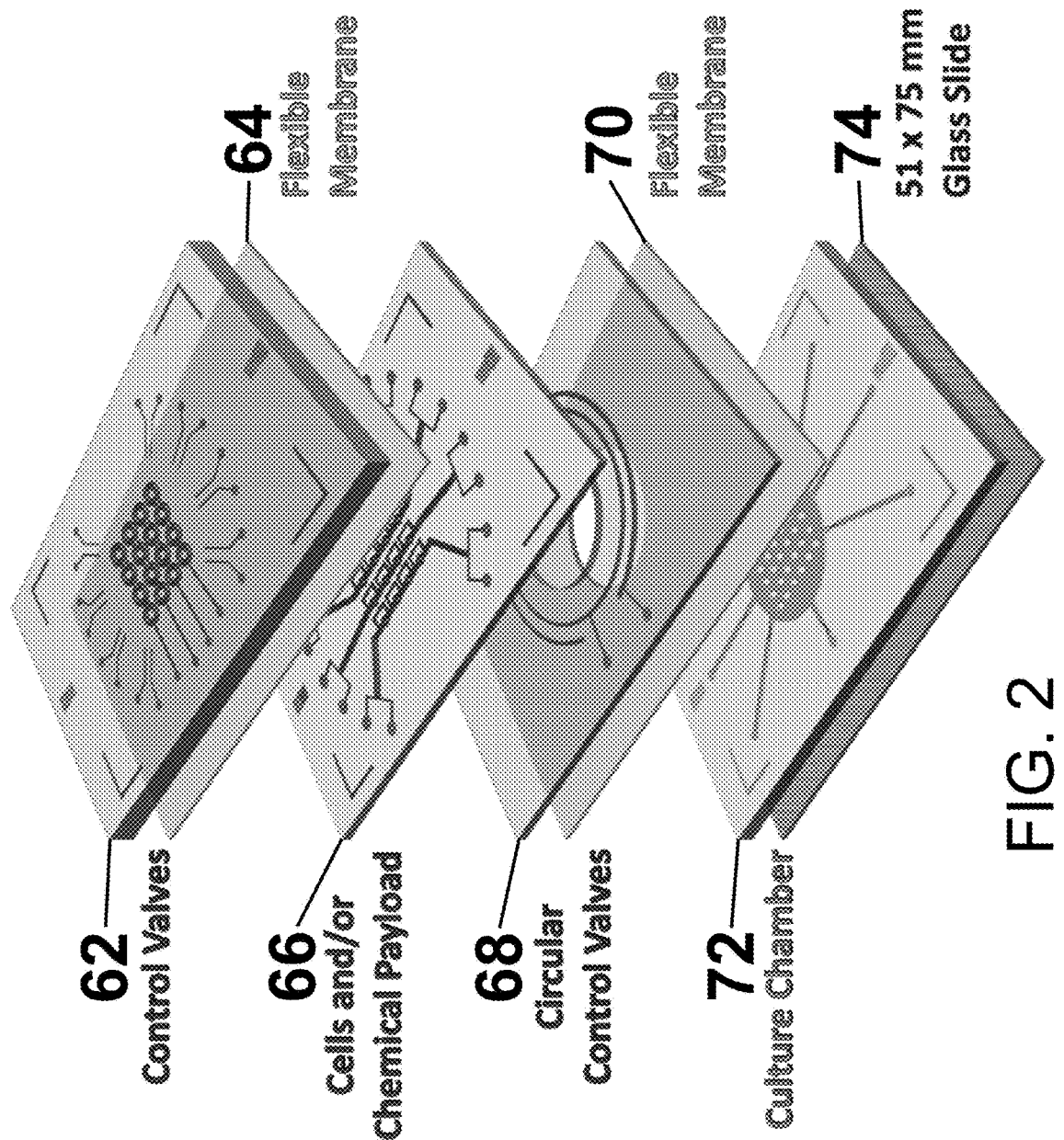
FIG. 2 illustrates an exemplary diagram showing how an addressable microfluidic plumbing system is created by stacking multiple layers, i.e., different layers, on top of each other, according to aspects of the present disclosure.

As mentioned before in reference to FIG. 1B, it should be understood that in some embodiments addressable microfluidic plumbing system 16 may include fewer or more than four layers. FIG. 2 illustrates an exemplary of an addressable microfluidic platform created with 7 different layers stacked on top of each other. The order of stacking and binding single layers form the multi-layered addressable microfluidic cell culturing platform may be as follows: 1) cells and/or chemical payload's control valve layer 62; 2) flexible membrane 64; 3) cells and/or chemical payload channels with addressable ports layer 66; 4) control valve layer for the culture chamber 68; 5) flexible membrane 70; 6) culture chamber 72; 7) substrate consisting of a glass slide, such as a 51×75 mm glass slide, 74 to which the device was bound using air plasma. A puncher (e.g., about 12 mm in diameter) or other similar device can be used to create the through hole at the center of control valve layer for the culture chamber 68 and flexible membrane 70 layers, in order to generate an interconnection between the payload layer and the culture chamber. The composition of flexible membranes 64 and 70 is not particularly limited, and non-limiting examples include Poly (ethylene glycol) diacrylate (PEGDA), Poly (octamethylene maleate (anhydride) citrate (POMaC), Poly (1,3-diamino-2-hydroxypropane-co-polyol sebacate) (APS), Poly(glycerol-co-sebacate) (PGS), Di-acrylated Pluronic F127F127-DA, combinations thereof, and the like. The thickness of the flexible membrane is not particularly limited and can be varied depending upon the particular arrangement and configuration of the microfluidic device. For example, a flexible membrane as used herein can be between about 25 to about 50 pm, about 30 to about 40 μm, about 30 to about 35 μm, ranges therebetween, or about 35 μm.

In an embodiment according to the present disclosure, localized chemo-release for interactive cells behavior control may be desirable. For example, closed-loop migration-control over single cells may be desirable. Specifically, with reference to FIG. 1B, controlling or influencing the behavior of individual cells disposed within cell culture chamber 32 may be desirable. To do so, a single-cell control platform may be used, which can be referred to as a "control-pixels". Each control-pixel may comprise one or more channels (FIG. 1B, 12), one or more -ports (FIG. 1B, 8), one or more valves (FIG. 1B, 10), one or more bypasses (FIG. 1B. 14) combination capable of releasing a chemoattractant in precise amounts, and at appropriate times. FIGS. 3A-3C illustrate an exemplary use of the addressable microfluidic plumbing system 16 (see FIG. 1B) demonstrating how localized chemo-release may be used in interactive cell migration control. For example, system 16 may include an array of addressable single-cell control-pixels 76 that may be used to control or modify the full range of the migratory behavior of cell 36 located within cell culture chamber 32 in FIG. 1B. In an exemplary embodiment, there may be at least one addressable port in each control-pixel. In an exemplary embodiment shown in FIG. 3A, control-pixels 76 are arranged'in a 3×3 array for illustrative purposes. An active pixel 76 may deliver a local chemoattractant signal 78 at different locations over time via a supply channel 80. As shown, 't' denotes time, and arrows indicate a direction in an intended cell path leading to a target 82. Target 82 may be determined by a practitioner (e.g., physician, scientist, or other suitable professional). Target 82 may be selected and/or used to influence a cell's movement in order to control cells, including but not limited to, during tissue generation (e.g. cell growth in a particular direction to grow a tissue organ). In FIG. 3A, control-pixel 76 is used to guide cell 36 along a chemical gradient (e.g. a circular illustrated path) to target 82. Local chemoattractant signals 78 are delivered in an addressable manner to each control-pixel 76 over time (e.g. $t_1$ to $t_f$). In these cases, the chemoattractant signals 78 may be released in front of cell 36 so that cell 36 may follow the chemoattractant signal accordingly.

In an exemplary embodiment, control-pixels 76 may also be used to trap cell 36 in place by rotating chemical gradients around cell 36. For example, as shown in FIG. 3B, chemoattractant signals 78 may be released around cell 36 at alternating locations and at various times. By controlling chemical gradients of chemoattractant 78 around cell 36 "rotating" gradients may be achieved. This gradient "rotation" may effectively lead cell 36 into a new direction with each new chemoattractant 78 release. In doing so, cell 36 may be "confused" into staying in one place; thus, stopping the cell from migrating in an unintended or undesirable direction.

Since chemoattractant signals may be transported by diffusion, and possibly also by convection, it may be desirable to minimize or avoid signal 78 crosstalk between adjacent control-pixels 76. For example, as shown in FIG. 3C, it may be desirable to avoid signal 78 crosstalk in multi-cellular trafficking. For pixels that are near each other in the addressable microfluidic plumbing system 16, chemoattractant 78 release amounts and duration may need to be optimized and/or monitored to minimize or avoid this effect.

In some embodiments the terms "control-pixel" and "address" may be used interchangeably.

The addressable microfluidic plumbing system 16 may also be designed to be scalable. For example, the addressable microfluidic plumbing system 16, including ports 22 and 24 like in FIG. 1B, may be designed to allow for optimal bio-manufacturing of organ-sized tissues. In order to bio-manufacture large tissue(s) using the addressable microfluidic plumbing system 16, the number of structures within system 16 (e.g., valves 26, channels 30, ports 22 and 24, chambers 32) would have to be numerous. To achieve this, multiple microfluidic arrays as described herein could be linked together to achieve a larger collection of arrays wherein those arrays would be linked via valves, channels, ports, and chambers in a manner that would be clear to one of skill in the art in view of this disclosure. In order to reduce any complexity and reliance on external hardware (which may be expensive), an object of this present disclosure is to maintain the design of the addressable microfluidic plumbing system 16 to be as minimalistic as possible, or as required. FIGS. 4A and 4B illustrate this point.

FIG. 4A shows an example of an addressable microfluidic plumbing configuration, illustrated using a 3×3 grid example, where an array of microfluidic ports is actuated via a separate channel 84 dedicated to each of the addresses 86. In this configuration, nine supply channels 84 may be required to deliver fluid to the individual nine different microfluidic ports 86. Moreover, a dedicated external hardware such as a pump, or solenoid valves, may be required in order to switch the fluid delivery to each address/port "on" and "off." For some applications, this approach may be less desirable because it may be less suitable for larger for applications because more complex arrangements may result in crowding.

FIG. 4B illustrates an exemplary addressable microfluidic plumbing that may comprise chemical-and-cell-payload channels 88 with addressable ports 86 and control-valve channels 90. An X+Y addressable approach is illustrated by FIG. 4B, where X and Y are the rows and columns of the exemplary addressable ports array. In an exemplary embodiment, X+Y scaling is achieved for scalability. As shown, only six channels (e.g., three chemical-and-cell-payload channels 86 and three control-valve channels 90) may be required in order to address nine chambers, as opposed to a total of 9 dedicated flow channels in the X*Y scaling in FIG. 4A. To lessen manufacturing costs and decrease plumbing complexity, this configuration may be desired. Moreover, the array displayed by FIG. 4B illustrates no crowding of the channels. No crowding of the channels may be desirable when creating arrays with a higher density of addresses (e.g., higher spatial resolution of the chemical or cell delivery and/or sampling). This approach may yield improved scalability. Therefore, by selecting an addressable array configuration with improved scalability, larger culture(s) or tissue(s) may be grown using the addressable microfluidic plumbing system 16 in FIG. 1B.

FIG. 4C shows the plumbing from FIG. 4B connected to a single culturing chamber or scaffold pore space 92. This utilization of the addressable microfluidic plumbing is different from the conventional implementations, which typically connect each addressable port to a separate chamber (e.g., high throughput drug screening in a multi microwell plate). Conversely, FIG. 4C illustrates how the addressable microfluidic plumbing can enable the localized nondestructive manipulation (i.e., delivery/probing) of cells and fluids within a single cultures or scaffold FIG. 5A illustrates a 3D microfluidic addressable cell culture or tissue scaffold 94, with cells 96, manufactured according to aspects of the present disclosure. In some embodiments, the 3D cell culture or tissue scaffold 94 may include 3D addressable microfluidic valves (e.g., ports, chambers, openings, etc.). The 3D microfluidic cell culture or tissue scaffold 94 may be fabricated using additive manufacturing (e.g., 3D printing, stereolithography, etc.). In one embodiment, the 3D microfluidic cell culture or tissue scaffold 94 may be formed by 3D bioprinting. 3D printing or 3D bioprinting may also be used to integrate addressable valves, ports, and/or chambers, as described according to aspects of the present disclosure, into 3D microfluidic cell culture or tissue scaffold 94. In an exemplary embodiment, 3D microfluidic cell culture or tissue scaffold 94 comprises microfluidic control valves and addressable ports 98 located at every corner of each control voxel (i.e., the 3D analogue of the 2D control pixel 76) inside a addressable plumbing network 100.

With reference to FIG. 5, in some embodiments the microfluidic control valves and addressable ports 98 may be fabricated by 3D printing and/or using a dissolvable 3D printed mold 102. Since microfluidic control valves and addressable ports 98 may include complex shapes, and may be small in size, 3D printing or 3D bioprinting (e.g. direct extrusion or stereolithography) and/or using, a dissolvable 3D printed mold/template of the valves may be desirable. In the present disclosure, a dissolvable 3D printed template of the microfluidic addressable plumbing network 100 with microfluidic control valves and addressable ports 98 may be produced from a dissolvable material (e.g. sugar), which may rigid enough to exist as a 3D network of 102 cylindrical filaments, but may also easily dissolve in water without toxic effects on surrounding cells 96.

A sugar template of a microfluidic addressable plumbing network 100 may be 3D printed to produce a structure as shown in FIG. 5B. Sugar template corresponds to the inverse of the desired microfluidic addressable plumbing network 100 shape to be printed (e.g., chemical-and-cells-payload channels 102 with microfluidic control valves and addressable ports 98). In a subsequent step, as shown in FIG. 5C the inverse template of the desired microfluidic addressable plumbing network 100 may be submerged into a hydrogel 104 or other suitable materials. The hydrogel 104 may solidify around the inverse template of the desired microfluidic addressable plumbing network 100. In a last step, and as shown in FIG. 5D, the inverse template of the desired microfluidic addressable plumbing network 100 may be dissolved and perfused out of the hydrogel 104 with water; thus, leaving the desired microfluidic addressable plumbing network 100 (e.g., chemical-and-cells-payload channels 102 with microfluidic control valves and addressable ports 98) within the hydrogel 104. As shown in FIG. 5A, the chemical-and-cells-payload carrying fluid may be perfused through 3D microfluidic tissue scaffold 94 at an input 106 and may exit at an output 108. The 3D microfluidic culture or tissue scaffold may be designed with at least one input and one output; however, the number of inputs and outputs within the plumbing network may be scalable if needed or to be proportional to the size of the desired scaffold.

A 3D microfluidic addressable cell culture or tissue scaffold 100 may include active microfluidic ports 98 for delivery of nutrients, oxygen, and/or chemical signals to cells throughout a 3D culture or scaffold 100. Additionally, the hydrogel 104 surrounding the addressable microfluidic plumbing networks 100 may be comprised of a transparent material. In doing so, cells and tissue growth within tissue scaffold 100 may be observed with microscopy, and further facilitate a better understanding of tissue growth. Lastly, 3D microfluidic addressable tissue scaffold d 100 may include an "addressable" array of structures (e.g., microfluidic valves and ports 98, channels 102, etc.) for localized chemical delivery and/or sampling; thus, resulting in improved cell control, tissue patterning, and tissue development monitoring, and according to aspects of the present disclosure described earlier.

In the foregoing embodiments of the present disclosure, an automated controller, or other suitable control, may be used to actuate the microfluidic valves.

In some embodiments, the addressable microfluidic culture or addressable microfluidic scaffold plumbing technology, disclosed by the present disclosure, may further comprise a pneumatic pumping system for operation and automated control of multi-layers addressable microfluidic cell culturing platforms. The automated pumping system may be actuated to automatically control the microfluidic addressable valves and ports disclosed by this disclosure. In some embodiments of the present disclosure, the automated pumping system may comprise a logic controller, such as an Ethernet-based programmable WAGO-I/O-SYSTEM 750 logic controller (See FIG. 6A), and an 8-channel digital output module (such as a WAGO Kontakttechnik GmbH and Co, Minden, Germany, Cat. #750-530) that allows the controller to actuate valves such as 24 V Festo (MH1-A-24VDC-N-HC-8V-PR-K01-QM-APBP-CX-DX, Festo, Germany, Cat. #197334) miniature pneumatic solenoid valves (See FIG. 6B). The solenoid valves may be connected to a custom DYI pneumatic pumping system (see FIG. 6C), which may be used to manipulate cells and fluids at the addresses. In some embodiments, valves capable of actuation and/or variable flow rates can be employed. In order to avoid contact between the solenoid valves and the pumped liquid, the system may contain machined reservoirs (see FIG. 6B) that prevent water from backing up into the pumped liquid. The solenoid valves may be actuated by sending 24 V signals to them via an eight-channel digital output module (Wago 750-530). The "on" and "off" positions of the solenoid valves may be corresponded to the "open" and "close" states of the valves 10 on the chip (see FIG. 1A). Switching from "open" to "close" means changing the pressure inside the on-chip valve from atmospheric pressure to a pressure that is around 13-25 psi, and ranges therebetween, respectively. The valves in control layers 26 (see FIG. 1B) may be also automatically actuated via miniature pneumatic solenoid valves that can be operated by a programmable controller such as a WAGO controller. A controller can be connected to a computer via an Ethernet interface or other suitable communication medium.

Figures 7A, 7B:
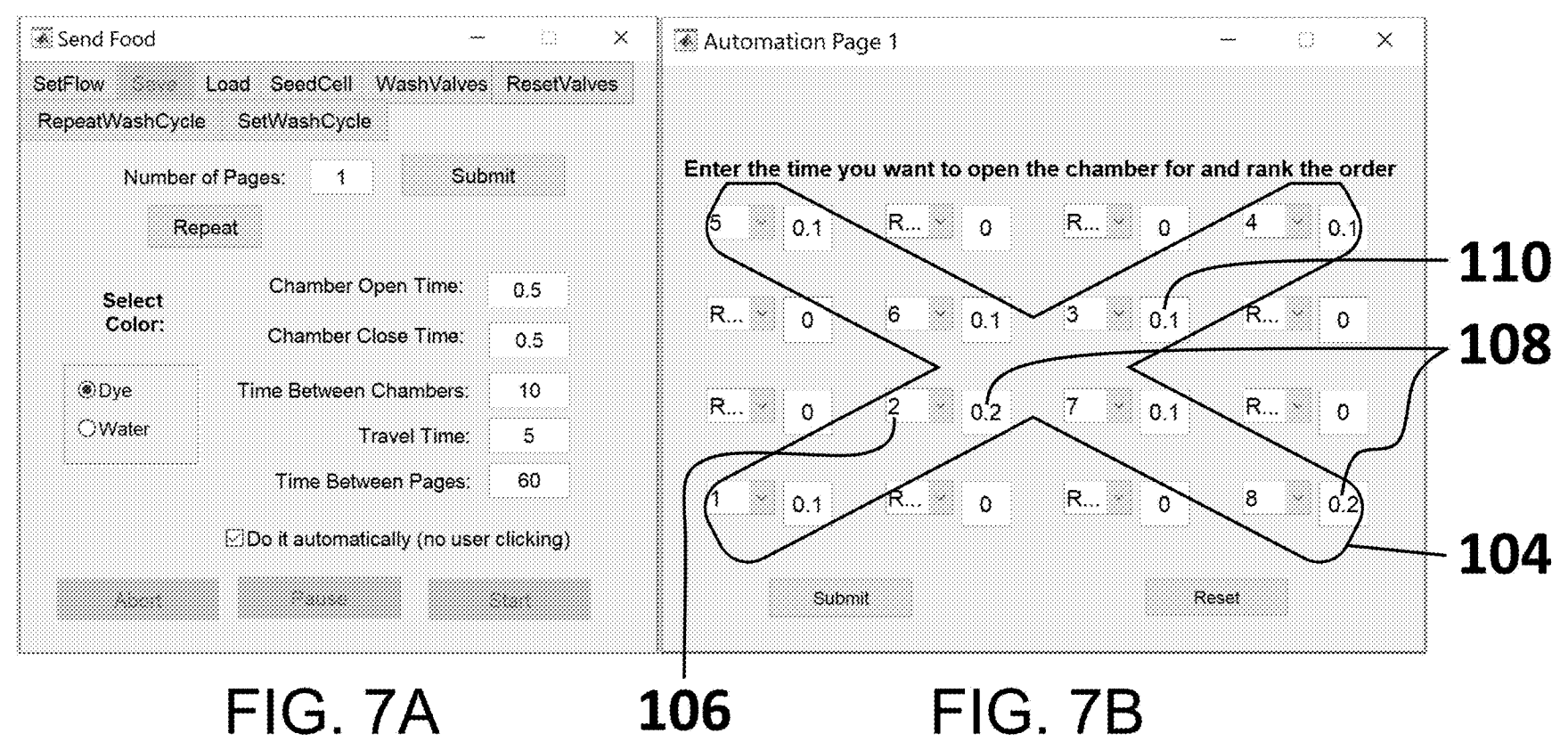
Figure 7C:
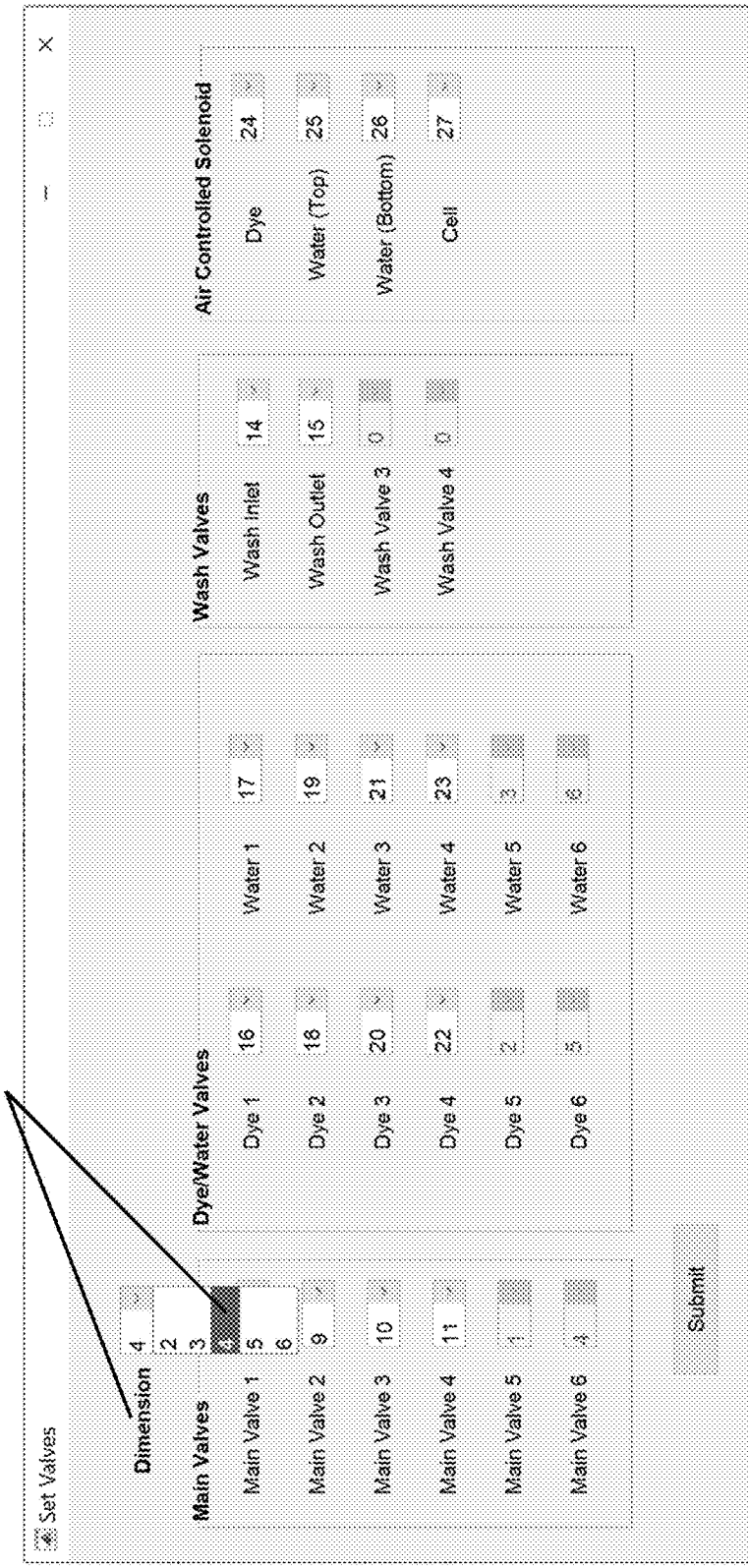

In an exemplary embodiment, by using a custom Matlab® graphical user interface (GUI) (see FIG. 7A), a sequence of patterns (e.g. "X" pattern 104 as shown in FIG. 7B) to be addressed on the system can be specified by a user. In some exemplary embodiments, the user may define the activating order of addressable ports 106 within the preset patterns and also in put the desired actuation time 108 and 110 for of each microfluidic valve. The actuation time of each microfluidic valves may be set differently, for example, the time box 108 is set to 0.2 seconds; while, the time box 110 is set to 0.1 seconds. Then these patterns are sent to a controller such as a WAGO module to toggle the solenoid valves in FIG. 6B, which in turn selectively actuated the on-chip valves at the preset locations (specified by the pattern created above) for the delivery of the payloads and collection of samples through the ports. FIG. 7C illustrates an exemplary GUI for setting the dimension 112 of the desired addressable ports array, which, in some embodiments, may be set to the dimension of 4×4 addressable ports 6 (as in FIG. 1A). It is understood that the dimension 112 of the addressable ports in the GUI may be changed to different dimensions and sizes: for example it may be set to work with 2D addressable microfluidic cell culturing platform that has the dimension of fewer or more than 4×4 addressable ports arrays 6; or it may be set to work with 3D addressable microfluidic tissue scaffold (e.g. fewer or more than 4×4×4 addressable ports arrays). As previously alluded to, pressure from the pumping system, including the valves, may be used to deliver chemical-and-cell payload-carrying fluid into the 2D or 3D microfluidic addressable cell culturing or tissue scaffold platforms. Alternatively, the pressure may be reversed to draw fluid from the 3D microfluidic system for microscopic analysis (e.g. tissue sample fluid from within a tissue scaffold to monitor cell growth or cell behavior).

According to the present disclosure, some possible fluid and/or cell manipulations within the culturing platform are: 1) seeding different cell types in varied amounts by flowing them into pre-determined spatial patterns; 2) nourishing the cells in the culture chamber by continuously renewing the media; 3) inducing and directing cell migration by establishing a dynamic nutrient and/or a chemoattractant gradient; 3) patterning tissue by modulating cell differentiation and/or morphology via delivery of bio-agonists (e.g. growth, differentiation factors) and/or drugs (e.g., cytoskeleton-altering) to specified locations/selected cells within the device; and 4) sampling a living culture non-disruptively by collecting and, sending off for analysis, effluents from different locations above the cells in the culture chamber.

Figures 8A, 8B:
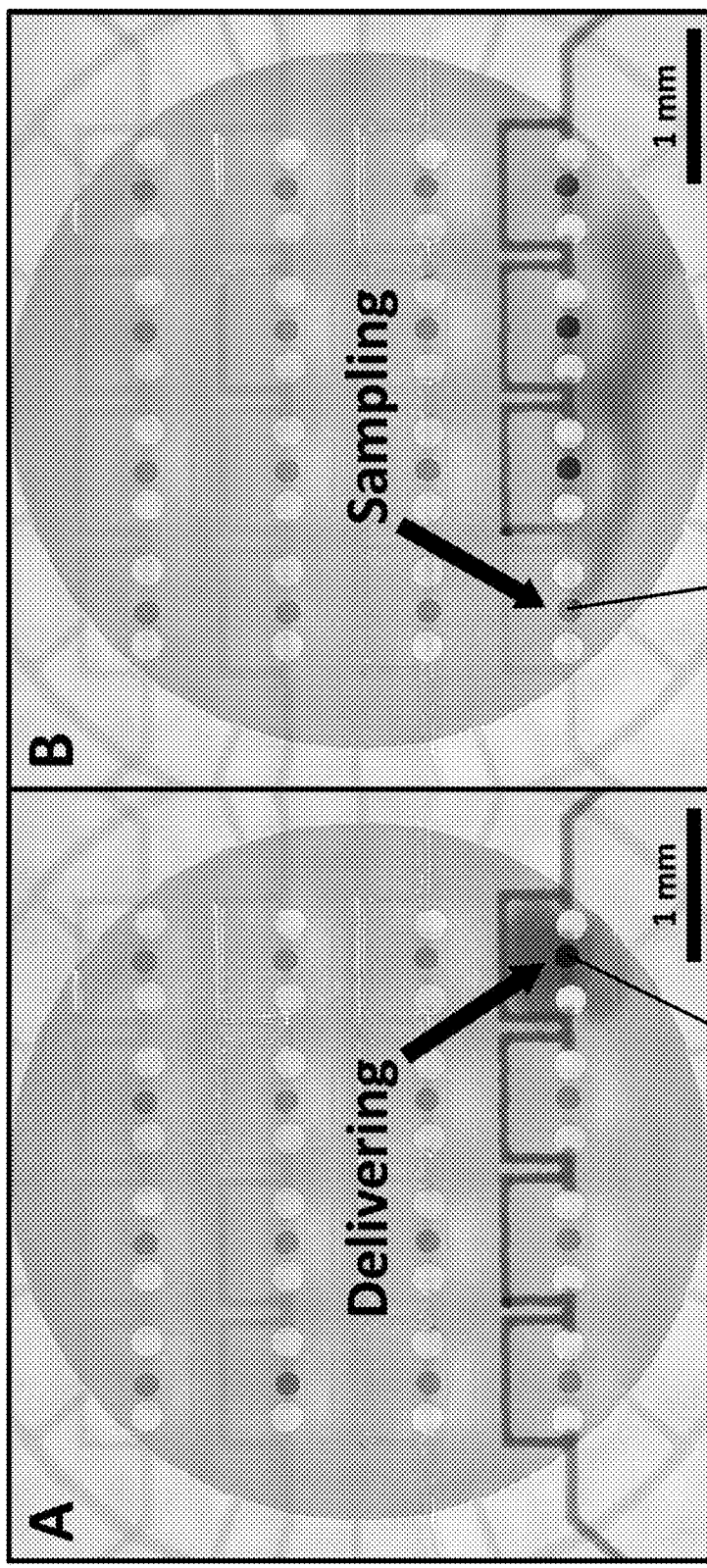
FIGS. 8A-8B illustrates an exemplary microscopy of the fluid manipulation, delivering and/or sampling, within the culture chamber, according to aspects of the present disclosure.

In an exemplary embodiment, the action of delivering and sampling chemicals within the addressable device is shown in the FIG. 8A and FIG. 8B, respectively. In FIG. 8A, a purple dye is delivered to the right bottom corner 114 of a 4×4 array of microfluidic ports; while in FIG. 8B, the same purple dye is withdrawn back via port 116 to the opposite end of the same address row. As a possible application, the picked-up fluid may be a cell culture effluent, which may be collected and then sent off to an external sensor for ex-situ analysis. This may eliminate the reliance on destructive chemical assays (e.g., histological sectioning or crushing the sample for plate reader analysis) ensuring continuous monitoring of the biology occurring within live cultures. Furthermore, this may be done continuously over long periods of time using automation and specifically programmed software protocols.

Using a configuration such as the one shown in FIGS. 1A and 1B, addressable microfluidic plumbing as described herein can be used to manipulate cells within a culture chamber 32 and ports 6 can be used for seeding (i.e., additive manufacturing) a co-culture of Mouse Bone Marrow-Derived Mesenchymal Stem Cells (MSCs) (S1502-100, strain: C57BL/6) and Mouse Embryo Fibroblasts (NIH/3T3) (ATCC® CRL-1658™, Strain: NIH/Swiss) in a predetermined spatial pattern. FIG. 9A shows an example of MSCs (white) seeded in a square shape 118 that surrounds the NIH/3T3s (gray) deposited in its center 120. Each of the addressable ports 6 (see FIG, 1A) in the exemplary 4×4 grid of may be used to deliver the different cell types to the culture chamber 32 below.

FIG. 9B demonstrates the addressable microfluidic plumbing system's ability to trap single cells 122 using O-valves 10 (see FIG. 1A) surrounding the microfluidic ports 8 (shown in FIG. 1A). It should be understood that, in principle, the addressable microfluidic plumbing system's improve over prior art systems by allowing for additive manufacturing (e.g., 3D printing) or cellular control with single cell precision. Machine vision-based automation may also be utilized to facilitate the aforementioned cellular control.

Figure 10A:
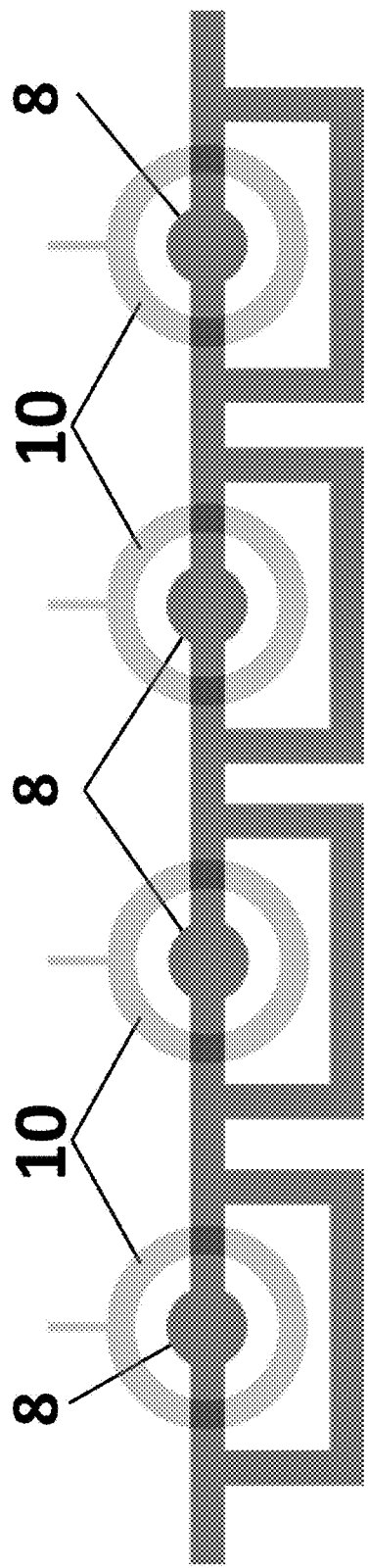
FIGS. 10A-10B illustrate an exemplary cell seeding, density gradient created by an exemplary system of the present disclosure demonstrating the utility of the technology described herein in additive manufacturing, according to aspects of the present disclosure.
Figure 10B:
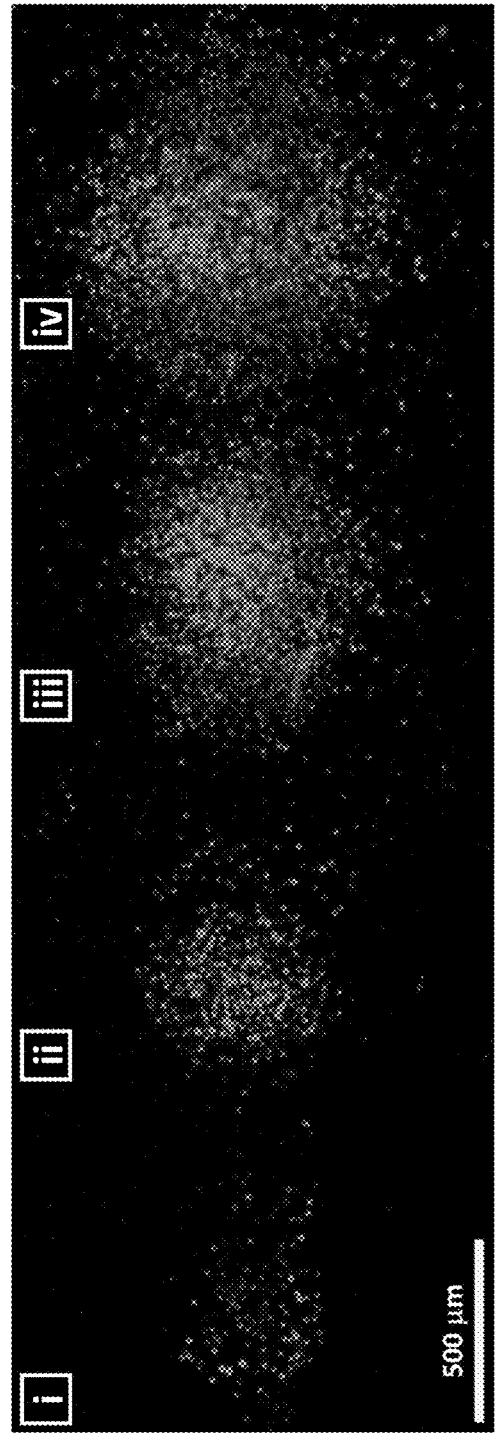

Cell seeding density may be controlled by varying the concentration of the cells in carrier fluid and by changing how much of the carrier fluid can pass through an address while the address is open. FIG. 10A illustrates a reference diagram showing a row of four addresses 8 that were used for creating the cell seeding density gradient pattern in FIG. 10B. This figure shows a cell density gradient created by delivering MSCs (gray) to the row of four addresses 8 in progressively increasing amounts, from left to right. This may be achieved by keeping the control valves 10 open for progressively longer times during the cell delivery via flow: starting with 0.5 seconds for the left-most address 8i and then increasing the interval by 0.5 second s for each subsequent location (ending with 2 seconds for the right-most one 8iv). Furthermore, the vertical distance between the addressable ports (e.g., such as the configuration of addressable ports 22 and 24 in FIG. 1B) and the substrate (i.e., the cell culture chamber's floor), and the height and the diameter of the ports may be modified to improve the resolution of cell patterning and accuracy in cell additive manufacturing. Lastly, the speed of the flow carrying the cell-and-chemical payload can be varied between the addresses as well.

Figure 11B:
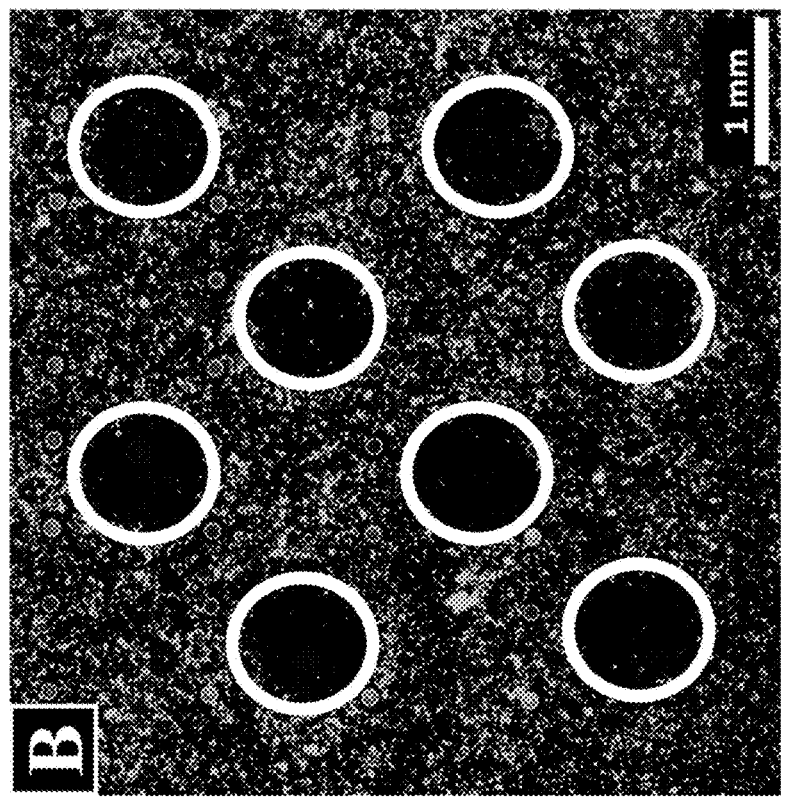
FIGS. 11A-11B illustrate an exemplary fluorescent microscopy of minimally-disruptive subtractive manufacturing, according to aspects of the present disclosure.
Figure 11A:
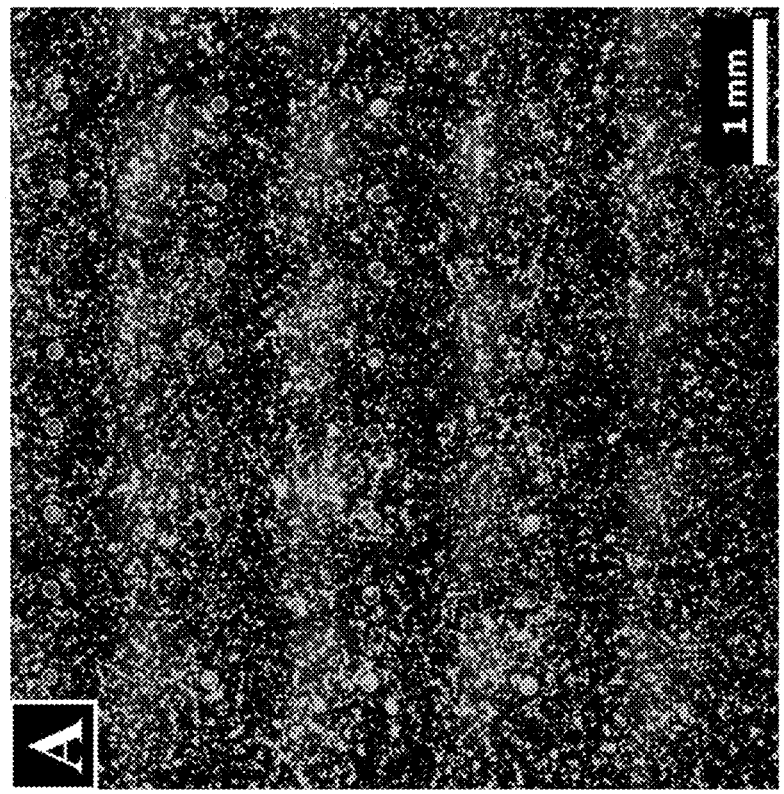

Additionally, FIG. 11 demonstrates the ability of embodiments of the systems described herein to create inverse cell patterns via subtractive manufacturing. This aspect of the present disclosure is not possible with bioprinters or prior art technology. In this embodiment, first, cells are seeded uniformly in the culture chamber 32 (see FIG. 1B), where are then allowed to adhere sufficiently to culture chamber floor in order to reach confluence, as shown in FIG. 11A. Subsequently, the focal adhesions anchoring the confluent cells to the bottom are cleaved from a culture surface by delivering a suitable digestive enzyme solution (e.g. a mixture of 0.25% Trypsin 0.2 g L-1 Ethylenediaminetetraacetic acid for a duration of 10 minutes). Eventually, the detached cells may be flushed away via flow of Phosphate-buffered saline (PBS) from user-specified addresses in order to create localized clearings arranged in a spatial pattern (marked with white circles) within the culture chamber 32 below the activated ports, as shown in FIG. 11B. It should be noted that the PBS flow can be, at times, pulsed to increase the detachment of the cells from the substrate.

This example of subtractive manufacturing demonstrates the ability of the improved systems described herein to remove undesired cell overgrowth and correct any localized seeding mistakes (something that is not possible with conventional scaffold and bioprinting approaches). Embodiments can also be used for contactless high throughput wound healing assays. Specifically, in a typical assay, it is desirable to be able to create an artificial "wound" opening in a monolayer of a patient's cells grown to confluence. Subsequently, the cells surrounding the wound proliferate and migrate, eventually covering, up the empty space and sealing the "injury". Typically, these wounds may be created using mechanical (e.g., scratch, stamp), thermal, electrical or optical damage to the cells. Most recently, flow focusing using microfluidics may have provided a contact-free alternative for selectively removing cells enzymatically, in order to generate a wound with a clear boundary and without damaging the surrounding cells or the substrate's surface coating (which is often necessary for increasing cell adhesion and/or directing the culture's fate). However, all of these assays yield only linear-shaped wounds, whereas embodiments of the present disclosure may be used to create circular wounds (such as those marked with white circles as in FIG. 11B)

Furthermore, embodiments of the present disclosure have the ability to perform minimally-disruptive cell biopsies at different locations in a culturing chamber. In embodiments of an addressable microfluidic platform, adherent cells may be detached from the adherence surface using the same procedure as in the subtractive manufacturing described above. However, in this case, they may be drawn into the above-positioned addressable port via pressure reversal and are carried away via flow to a location outside of the culture chamber 32 via the microfluidic channels. Subsequently, ex-situ sacrificial analysis can be performed on the collected cells without affecting the main culture in certain embodiments.

The improved fluid and cell manipulation abilities of the embodiments described herein demonstrate the versatility and capability to perform automated minimally-disruptive observations within living cultures, which was previously unattainable.

According to aspects of the present disclosure, fabrication of master molds used in soft lithography, which can be composed of micron-sized features of the 2D addressable microfluidic system, can utilize standard photolithography procedures, such as spin coating, UV exposure and developing. However, embodiments of exemplary multi-layered master mold of the chemical and cell payload channels with addressable microfluidic ports d iffier from prior art manufacturing techniques in that embodiments may be fabricated using both negative photoresist (SU8) and positive photoresist (AZ® P4620) to generate two different heights and/or profiles (round and square) of micron-sized features on a 4-in silicon wafer, as shown in FIG. 12. First, a microscale pattern may be sketched using AutoCAD (Autodesk, Mill Valey, Calif.) and printed at 50,800 dpi on a transparency (Fineline Imaging, Colorado Springs, Colo.) to generate a high-resolution photomask. Four-inch silicon wafers (or similar size) may be washed carefully with diluted soap, then rinsed with a mixture of acetone, methanol and DI-water (AMD solvents). The rinsed wafers may then be dehydrated at about 180° C. for about 15 minutes. Subsequently, the wafers may be cooled down to room temperature and treated with Hexamethyldisilane to enhance the photoresist adhesion. As shown in FIG. 12A, the positive photoresist AZ® P4620 template is first created, and the developed photoresist is then reflowed by baking the wafer at 150° C., in order to achieve the round profile features. Alignment marks are also imprinted on the two sides of the wafer, in order to be used in the next step. FIG. 12B shows the SU-8 photoresist layer patterned on the same wafer. Prior to the UV exposure, the alignment marks on the template photomask and on the silicon wafer are aligned using a custom mask aligner.

In an optional step in the exemplary process, the wafer may be treated with a silane surface treatment to reduce the surface energy and to more easily lift off any PDMS from the wafer. This step may be recommended for completed master molds. In the optional silane surface treatment step, under a fume hood, a cap from a trichloro (1H,1H,2H,2H-perfluorooctyl) silane bottle may be removed, and placed inside a glass vacuum desiccator. Next, the completed, patterned wafer may be transferred into the desiccator. Once the desiccator is closed, a vacuum may be applied for about three minutes. After about three minutes, the vacuum is turned off. The wafer may then be exposed to the silane vapor for approximately 30 minutes.

The process may include a number of steps, but it will be understood that additional or alternative steps may be added or substituted depending numerous factors including, but not limited to, particular microfluidic device being used, material selection (e.g., type of biomaterial), desired application, or other factors.

It should be understood that the exemplary microfluidic fabrication steps and processes described above are not limited to the order as described. The microfluidic devices, and associated components, may be fabricated using any number of steps or processes according to aspects of the present disclosure without regard to any single particular sequence.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

What is claimed is:

1. A microfluidic plumbing system comprising:
an array of addressable microfluidic ports that include a plurality of inlet ports and that serve as access openings that allow fluid flow to and from different locations associated with a cell culture chamber;
an inflatable on-chip valve layer comprising inflatable on-chip valves, wherein the inflatable on-chip valves are addressable and are able to be actuated to open or closed states, which allow or block fluid flow to and from individual addressable microfluidic ports from among the array of addressable microfluidic ports;
one or more flexible membrane layers disposed adjacent the inflatable on-chip valve layer;
one or more fluid flow layers disposed adjacent the one or more flexible membrane layers, wherein the array of addressable microfluidic ports are disposed within the one or more fluid flow layers and wherein each addressable microfluidic port defines a path for fluid flow; and
a cell culture chamber that is not a multi microwell plate and that is located adjacent the one or more fluid flow layers and in fluid communication with the array of addressable microfluidic ports;
wherein the cell culture chamber defines a single culturing chamber or scaffold pore space in fluid communication with at least two of the plurality of inlet ports included in the array of addressable microfluidic ports; and
wherein the array of addressable microfluidic ports deliver fluid flow to or from one or more selected locations within the single culturing chamber or scaffold pore space.

2. The microfluidic plumbing system of claim 1, wherein, when an addressable on-chip valve is in the open state, a flexible membrane associated with the one or more flexible membrane layers in proximity to the corresponding addressable on-chip valve is deflated, thereby allowing fluid exchange between the one or more fluid flow layers and the cell culture chamber via corresponding one or more addressable microfluidic ports.

3. The microfluidic plumbing system of claim 1, wherein, when an addressable on-chip valve is in the closed state, a flexible membrane associated with the one or more flexible membrane layers in proximity to the corresponding addressable on-chip valve is inflated to create a barrier, thereby preventing fluid exchange between the one or more fluid flow layers and the cell culture chamber from occurring via the corresponding one or more addressable microfluidic ports.

4. The microfluidic plumbing system of claim 1, wherein the access openings defined by the array of addressable microfluidic ports are offset from each of the corresponding inflatable on-chip valves.

5. The microfluidic plumbing system of claim 1, further comprising one or more cell layers that comprise living cells situated in or on the cell culture chamber.

6. The microfluidic plumbing system of claim 1, wherein fluid flow carries a payload and wherein the payload includes chemicals.

7. The microfluidic plumbing system of claim 1, wherein fluid flow carries a payload and wherein the payload includes cells.

8. The microfluidic plumbing system of claim 1, wherein the fluid flow carries a payload and wherein the payload modulates culture development in the cell culture chamber.

9. The microfluidic plumbing system of claim 1, wherein the fluid flow carries a payload and wherein the payload is adapted to sample cells from the cell culture chamber.

10. The microfluidic plumbing system of claim 1, wherein the fluid flow carries a payload and wherein the payload is adapted to sample fluids from the cell culture chamber.

11. The microfluidic plumbing system of claim 1, wherein the cell culture chamber defines an upper plane, and wherein the array of addressable microfluidic ports operates in a 2D plane corresponding to the upper plane of the cell culture chamber.

12. The microfluidic plumbing system of claim 1, wherein the cell culture chamber defines an upper plane, one or more walls and a floor plane, and wherein the array of addressable microfluidic ports operates in multiple 2D planes surrounding the cell culture chamber and corresponding to at least one of the upper plane, the one or more walls and the floor plane of the cell culture chamber.

13. The microfluidic plumbing system of claim 1, wherein the array of addressable microfluidic ports are adapted to control or modify behavior of cells located in the cell culture chamber.

14. The microfluidic plumbing system of claim 13, wherein an addressable microfluidic port from among the array of addressable microfluidic ports delivers a local chemical signal at different locations of the cell culture chamber over time.

15. The microfluidic plumbing system of claim 13, wherein an addressable microfluidic port from among the array of addressable microfluidic ports traps one or more cells in place by rotating chemical gradients around the one or more cells.

16. The microfluidic plumbing system of claim 15, wherein the one or more cells is trapped by releasing chemoattractant signals around the one or more cells at alternating locations and at different times.

17. The microfluidic plumbing system of claim 1, further comprising a substrate upon which the cell culture chamber is positioned.

18. The microfluidic plumbing system of claim 17, wherein the substrate is transparent.

19. The microfluidic plumbing system of claim 18, wherein the transparent substrate is a glass slide.

* * * * *